United States Patent [19]
Menchen et al.

[11] Patent Number: 5,468,365
[45] Date of Patent: * Nov. 21, 1995

[54] VISCOUS ELECTROPHORESIS POLYMER MEDIUM AND METHOD

[75] Inventors: Steven M. Menchen, Fremont, Calif.; Mitchell A. Winnik, Toronto, Canada; Ben F. Johnson, Palo Alto, Calif.

[73] Assignee: Applied Biosystems, Inc., Foster City, Calif.

[ * ] Notice: The portion of the term of this patent subsequent to Mar. 1, 2011, has been disclaimed.

[21] Appl. No.: 125,623

[22] Filed: Sep. 22, 1993

Related U.S. Application Data

[63] Continuation-in-part of Ser. No. 950,863, Sep. 24, 1992, Pat. No. 5,290,418.

[51] Int. Cl.⁶ .................................................. C25B 7/00
[52] U.S. Cl. ............................ 204/299 R; 204/182.8; 524/504; 524/505; 524/507; 524/520
[58] Field of Search .................. 204/299 R, 182.8; 524/505, 520, 507, 504

[56] References Cited

U.S. PATENT DOCUMENTS

| | | | |
|---|---|---|---|
| 3,779,970 | 12/1973 | Evani et al. | 260/29.6 RW |
| 4,079,028 | 3/1978 | Emmons et al. | 260/29.6 NR |
| 4,079,029 | 3/1978 | Gross | 260/29.6 TA |
| 4,170,539 | 10/1979 | Simmons | 204/295 |
| 4,209,333 | 6/1980 | Ong et al. | 106/25 |
| 4,426,485 | 1/1984 | Hoy et al. | 524/591 |
| 5,164,055 | 11/1992 | Dubrow | 204/180.1 |
| 5,164,057 | 11/1992 | Mori et al. | 204/299 R |
| 5,290,418 | 3/1994 | Menchen et al. | 204/299 R |

OTHER PUBLICATIONS

Dibbs, M. G., et al., "Studies of the dilute solution conformational dynamics of homopolymer stars and combs via oscillatory flow biregringence and viscoelasticity," *Chemical Abstracts* 99:176663b (1983) No Month Indicated.

Domszy, R. C., et al., "Thermoreversible Gelation and Crystallization of Homopolymers and Copolymers," *Macromolecules* 19:310–325 (1986) No Month Indicated.

Kumakura, M., et al., "Properties of thermolysin immobilized in polymer matrix by radiation polymerization," *Chemical Abstracts* 100:117169m (1984) No Month Indicated.

Luckey, J. A., et al., "High Speed DNA Sequencing by Capillary Electrophoresis," *Nucleic Acids Research* 18(15):4417–4421 (1990) No Month Indicated.

Russo, P. S., "A Perspective on Reversible Gels and Related Systems," Chapter 1 from *Reversible Polymeric Gels and Related Systems* (Russo, P. S., ed., American Chemical Society, Washington, D.C., 1987) No Month Indicated.

Sogah, D. Y., "Ladders, stars, and combs by a group-transfer polymerization," *Chemical Abstracts* 109:190949f (1988) No Month Indicated.

*Primary Examiner*—John Niebling
*Assistant Examiner*—C. Delacroix-Muirheid
*Attorney, Agent, or Firm*—Peter J. Dehlinger; Vincent M. Powers

[57] ABSTRACT

A viscous electrophoresis separation medium is disclosed. The medium is formed by a matrix formed by a copolymer composed of hydrophilic polymer segments having selected, substantially uniform segment lengths, and a plurality of hydrophobic polymer segments carried on, and spaced from one another by the hydrophilic polymer segments. Also disclosed is an electrophoresis method which employs the separation medium, and novel copolymers used in forming the medium.

28 Claims, 21 Drawing Sheets

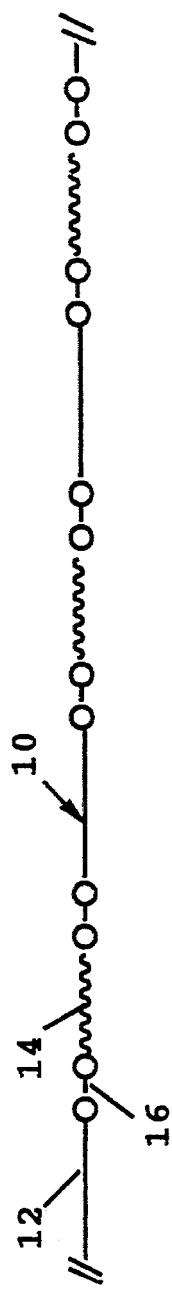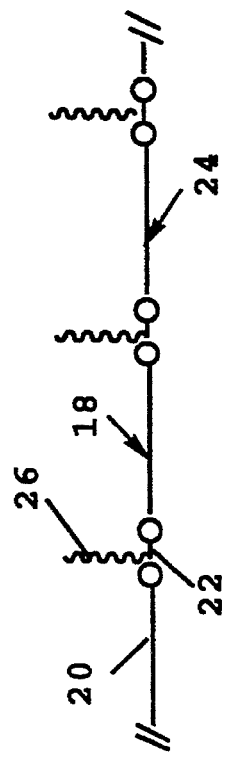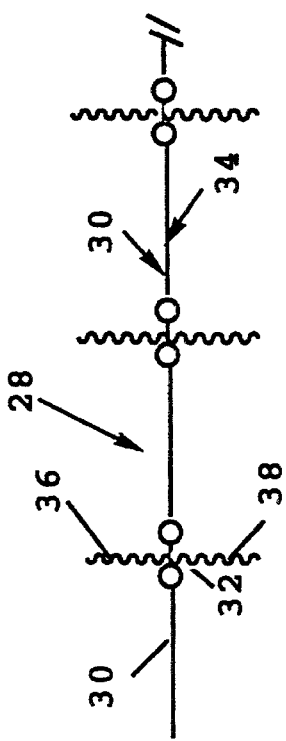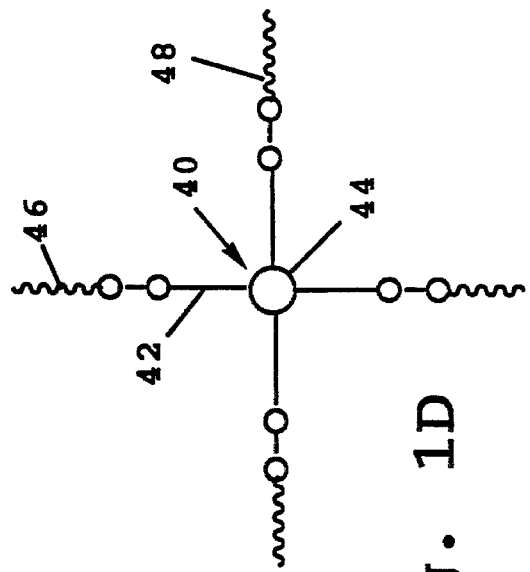
Fig. 1A
Fig. 1B
Fig. 1C
Fig. 1D

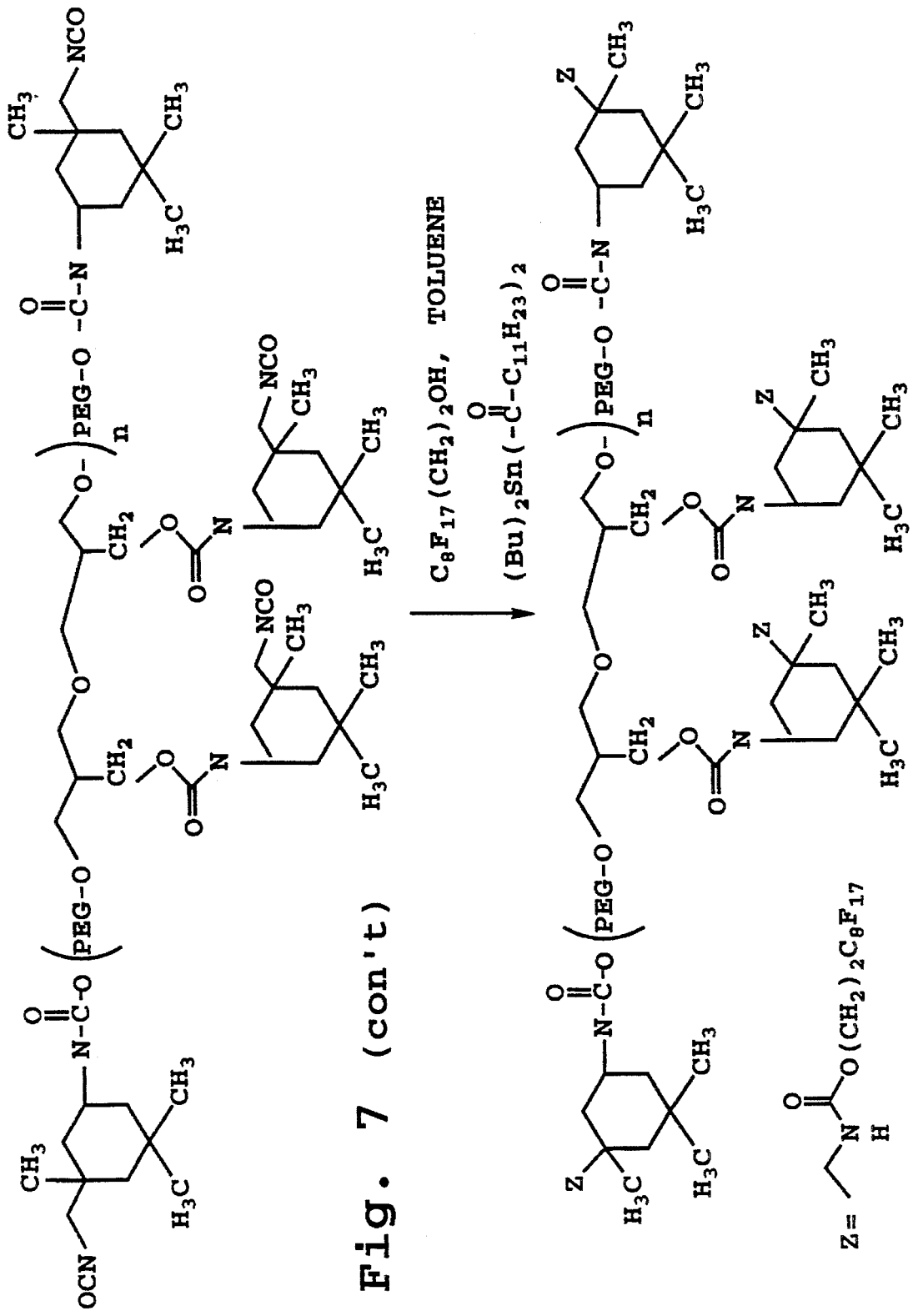
Fig. 7 (con't)

VISCOUS ELECTROPHORESIS POLYMER MEDIUM AND METHOD

This application is a continuation-in-part of U.S. patent application Ser. No. 07/950,863 filed Sep. 24, 1992, U.S. Pat. No. 5,290,418.

FIELD OF THE INVENTION

The present invention relates to polymer media for use in electrophoretic separations of biomolecules, and in particular, to media compatible with capillary electrophoresis separation techniques.

REFERENCES CITED

Cohen, A., et al., Anal Chem, 59:1021 (1987).

Cohen, A., et al., J. Chromatography, 458:323 (1988).

Compton, S., et al., BioTechniques, 6(5):432 (1988).

Kaspar, T., et al., J Chromatography, 458:303 (1988).

Malik et al., *J. Org. Chem.*, 56:3043 (1991).

Maniatis, T. et al., "Molecular Cloning: A Laboratory Manual," Cold Spring Harbor Labs (1982).

Stryer, L., *Biochemistry*, 3rd ed., W. H. Freeman & Company, New York, pp. 44–48 (1988).

BACKGROUND OF THE INVENTION

Gel electrophoresis is a powerful method of separating large biomolecules, such as proteins, deoxyribonucleic acids (DNA), and ribonucleic acids (RNA). In gel electrophoresis, a mixture of biomolecules is placed on a selected gel medium and the gel is subjected to an external electric field. The velocity (v) of migration of a biomolecule through the gel depends on the strength of the electric field (E), the net charge (z) on the molecule, and the frictional coefficient (f) of the medium:

$$v = Ez/f$$

The frictional coefficient depends on the mass and shape of the molecule and the viscosity of the medium.

Gels have become the preferred medium for conducting electrophoretic separations because they suppress the convective currents produced by small temperature gradients in less viscous media, and they act as molecular sieves which inhibit movement of large molecules, but permit smaller molecules to move readily through the pores of the gel. Polyacrylamide gels have generally been the medium of choice for performing separations because they are chemically inert and their pore sizes can be controlled by selection of a desired ratio of acrylamide and methylenebisacrylamide (cross-linking agent), and total monomer concentrations used in polymerization. The polyacrylamide gel is typically generated by free radical polymerization of the component monomers, using a free radical initiator, in the presence of the electrophoresis medium.

Electrophoretic separations of proteins are often performed in a cross-linked polyacrylamide gel under protein denaturing conditions. For example, proteins can be dissolved in a detergent solution, e.g., sodium dodecyl sulfate (SDS), and subjected to mercaptoethanol or dithiothreitol treatment to reduce any disulfide bonds. The SDS anions bind to the protein at a ratio of about one SDS molecule to two amino acid residues, thereby imparting a large net negative charge and bulk to the denatured protein. The charge and bulk of the protein-SDS complex are roughly proportional to the mass of the native protein. Displacements of a protein or peptide within a gel matrix can thereby be related to molecular size on a basis of the size and charge on the molecule. In the case of nucleic acids, which have roughly the same charge density, displacement in the gel matrix is more directly related to molecular size.

Electrophoresed complexes are usually visualized by staining with a dye, such as Coomassie blue, or by autoradiography when the molecules are radioactively labelled. The displacement of a biomolecule in the gel is nearly linearly proportional to the logarithm of the mass of the molecule, with exceptions found for such species as glycosylated and membrane proteins. Proteins differing by as little as 2% in mass can often be distinguished by electrophoresis (see, generally, Stryer, L.).

One electrophoretic technique that permits rapid, high-resolution separation is capillary electrophoresis (CE) (Cohen, 1987, 1988, Compton, Kaspar). In one CE procedure, a capillary tube is filled with a fluid electrophoresis medium and the fluid medium is crosslinked or temperature-solidified within the tube to form a non-flowable, stabilized separation medium. A sample volume is drawn into or added to one end of the tube, and an electric field is applied across the tube to draw the sample through the medium. Typically, a bioseparation conducted by CE employs fused silica capillary tubes having inner diameters between about 50–200 microns, and ranging in length between about 10–100 cm or more.

The polymer concentration and/or degree of cross-linking of the separation medium may be varied to provide separation of species over a wide range of molecular weights and charges. For example, in separating nucleic acid fragments greater than about 1,000 bases, one preferred temperature-solidified material is agarose, where the concentration of the agarose may vary from about 0.3%, for separating fragments in the 5–60 kilobase size range, up to about 2%, for separating fragments in the 100–3,000 basepair range (Maniatis). Smaller size fragments, typically less than about 1,000 basepairs, are usually separated in cross-linked polyacrylamide. The concentration of acrylamide polymer can range from about 3.5%, for separating fragments in the 100–1,000 basepair range, up to about 20%, for achieving separation in the 10–100 basepair range. For separating proteins, crosslinked polyacrylamide at concentrations between about 3–20% are generally suitable. In general, the smaller the molecular species to be fractionated, the higher is the concentration of crosslinked polymer required.

The resolution obtainable in solidified electrophoresis media of the type described above has been limited, in the case of small molecular weight species, by difficulties in forming a homogeneous, uniform polymer matrix at high polymer concentration within an electrophoresis tube, and especially within a capillary tube. In one general method for forming a high-concentration solidified matrix in a tube, a high-concentration polymer solution, in a non-crosslinked, low-viscosity form, is introduced in fluid form into the tube. The fluid material is then crosslinked, for example, by exposure to light in the presence of persulfate and a cross-linking agent.

At high polymer concentrations, reaction heat gradients formed within the tube tend to produce uneven rates of reaction and heat turbulence which can lead to matrix inhomogeneities. Also, entrapped gas bubbles generated during the crosslinking reaction produce voids throughout the matrix. The non-uniformities in the matrix limit the degree of resolution that can be achieved, particularly among closely related, small molecular weight species.

These problems may be overcome by polymerizing the gel material at elevated pressure; however, producing a controlled pressure within a capillary gel introduces difficult technical problems.

In the case of temperature-solidified gels, a polymer is introduced into an electrophoresis tube in a fluid form, then allowed to gel to a solid form by cooling within the gel. This approach, however, is generally unsuitable for fractionating low molecular weight species, such as small peptides and oligonucleotides, since the polymers, such as agar and agarose, that are known to have the necessary temperature-solidifying setting properties are not effective for fractionating low molecular weight species, even at high polymer concentrations.

A second limitation associated with crosslinked or temperature solidified matrices is the difficulty in removing crosslinked gel matrix from the gel support. In the case of a capillary-tube support, this may prevent recovery of separated material within the gel, and also may prevent reuse of the capillary tube.

Isoelectric focusing (IEF) is another separation method based on the migration of a molecular species in a pH gradient to its isoelectric point (pI). The pH gradient is established by subjecting an ampholyte solution containing a large number of different pI species to an electric field. Biomolecules added to the equilibrated ampholyte solution will migrate to their isoelectric points along the pH gradient. The components can then be isolated by eluting the gradient and capturing selected eluted fractions.

Although IEF methods are usually carried out in a low-viscosity fluid medium, it is occasionally advantageous to perform the IEF separation in a stabilized matrix. Crosslinked or temperature-stabilized gels of the type described above have been employed in IEF methods, but present some of the same limitations noted above for electrophoretic methods. In particular, the stabilized gels are generally not removable from capillary tubes, and isolating separated molecular species from the matrix may be inconvenient because exhaustive dialysis or electroelution are required.

SUMMARY OF THE INVENTION

The present invention includes, in one aspect, an electrophoresis separation medium which comprises a matrix of aggregated regular, alternating copolymers in an aqueous medium. The copolymers are composed of hydrophilic polymer segments having selected, substantially uniform segment lengths, and a plurality of hydrophobic polymer segments carried on and spaced from one another by the hydrophilic polymer segments. The medium is characterized by (i) the ability of the medium to effect a high-resolution electrophoretic separation of biopolymer molecules in a defined molecular size range, and (ii) a concentration of the copolymer which is above the interpolymeric-aggregation transition concentration, defined by the concentration of copolymer at which a marked rise in viscosity of an aqueous dispersion of the copolymer is observed.

The copolymers may have one of the following structures:

(a) a comb or tuft copolymer structure in which the hydrophobic polymer chains extend outwardly from a backbone composed of linked hydrophilic polymer segments;

(b) a block copolymer structure having an alternating linear sequence of the hydrophilic segments and hydrophobic segments; and (c) a star copolymer structure in which the hydrophobic polymer chains are carried at the distal ends of the hydrophilic polymer segments which are attached at their proximal ends to a common anchor.

The hydrophilic polymer segments are preferably polyether (e.g., polyethylene oxide), polyester (e.g., polyglycolic acid or polylactic acid), polysaccharide, polyurethane, polyamides, polysulfonamide, or polysulfoxide, and the polymer segments may be joined by linking moieties to which the hydrophobic polymer segments are attached to the linking moieties.

In one preferred embodiment, the copolymer is a comb copolymer structure composed of a backbone structure formed of polyethylene oxide segments, and segments in which fluorinated hydrocarbon segments extend outwardly from a backbone composed of linked polyethylene oxide segments.

In another preferred embodiment, the copolymer is a star copolymer, where the copolymers are formed of contiguous linear hydrophilic polymer segments having a selected combined length, and hydrophobic polymer segments attached at each of the free ends of the joined hydrophilic segments(s). The hydrophilic polymer segments may be formed from two hydrophilic segments joined at their adjacent ends by a common anchor, or formed of a single linear polymer chain.

Also disclosed is an electrophoresis system for separating biopolymers. The system includes a support defining an elongate channel connectable at opposite ends to opposing polarity terminals of a voltage source, and contained within the channel, an electrophoresis separation medium of the type described above.

In another aspect, the invention includes a method for fractionating a mixture of biopolymer molecules in a selected size range within a matrix contained in a support. The method includes the steps of selecting a copolymer of the type described above having selected length hydrophilic polymer segments, and dispersing the copolymer in an aqueous concentration, at a copolymer concentration which is above the interpolymeric-aggregation transition concentration, thereby forming a matrix having a substantially uniform mesh size. The matrix is placed within a support having an elongate channel connectable at opposite ends to opposing polarity terminals of a voltage source.

The mixture of biopolymer molecules is added to the matrix at one end of the support, and electrophoretic separation is carried out across the ends of the support.

In one embodiment, the method is used for electrophoretic separation of DNA fragments within a selected size range, where the copolymers have a comb structure having a backbone composed of linked hydrophilic segments and hydrophobic segments spaced at substantially equal intervals along the backbone, at a selected distance between about 50 and 1,000 backbone chain atoms, for fractionation of DNA fragments in selected size ranges (i) of less than about 100 basepairs, at a selected backbone spacing of about 100 chain atoms, (ii) of greater than about 1,000 basepairs, at a selected backbone spacing between about 500–1,000 chain atoms, and (iii) of sizes between about 100–1,000 basepairs at a selected backbone spacing between about 100–800 chain atoms.

In another embodiment, for use in achieving single-base resolution of single-stranded DNA fragments of between about 30 and about 200 bases in length, and preferably between about 30 and about 400 bases in length, or greater, the copolymers are formed of contiguous linear hydrophilic polymer segments having a selected combined length of between about 100–4,000 backbone atoms, and hydrophobic polymer segments attached at each of the free ends of the hydrophilic segment(s).

Also disclosed are novel copolymers formed of a polymer structure composed of hydrophilic polymer segments having substantially uniform segment lengths, and a plurality of hydrophobic fluorinated hydrocarbon polymer segments carried on the polymer structure and spaced from one another by the hydrophilic polymer segments, and synthetic methods of forming the polymers.

These and other objects and advantages of the invention will become more fully apparent when the following detailed description of the invention is read in conjunction with the accompanying drawings.

DESCRIPTION OF THE DRAWINGS

FIGS. 1A–1F are schematic illustrations of copolymers having a block copolymer (FIG. 1A), a comb copolymer (FIG. 1B), a tuft copolymer (FIG. 1C), and a star copolymer (FIGS. 1D–1F) architecture;

DETAILED DESCRIPTION OF THE INVENTION

Figure 1E:
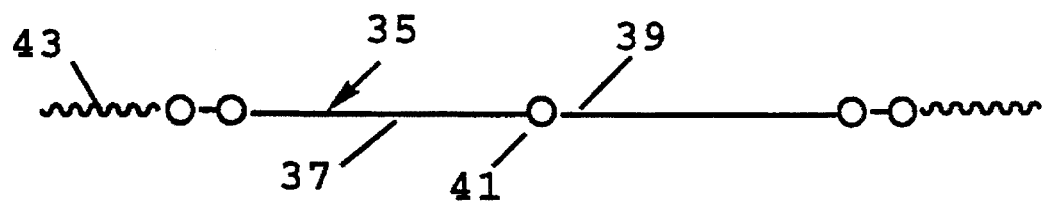

The following discussion describes the invention in further detail and illustrates the invention by way of certain examples.

I. Definitions

The following terms, as used herein, have the meanings as indicated:

"Aqueous dispersion medium" refers to an aqueous-based medium that serves to disperse materials dissolved or suspended in it.

"Association colloid", as used herein, refers to a dispersion of particles (e.g., micelles) of one substance in another, e.g., water, in which the particles are formed by the association or aggregation of molecules having both hydrophilic and hydrophobic regions.

"Chain-reaction polymerization" or "addition polymerization" refers to a polymerization process in which each monomer addition to a growing polymer chain depends upon a preceding reaction.

"Copolymer" refers to a polymer composed of more than one kind of monomeric unit in the same molecule. Copolymers are generally characterized as "block copolymers," in which case polymer segments of one monomer type alternate with polymer segments of another monomer type, or they can be "graft copolymers," in which case a polymer segment having one composition is chemically grafted as one or more branches onto a chain having a different composition. Such block and graft copolymers can have groups pendant from a polymer backbone composed of the monomers and the copolymers can be joined to a common anchor. A combination of block and graft sections can also be present in one copolymer molecule.

"Hydrophilic polymer segment" refers to a polymer segment which is soluble in an aqueous medium. A copolymer composed in part of a hydrophilic polymer segments and part hydrophobic polymer segments has a tendency to dissolve in an aqueous medium, with the hydrophobic polymer segments of different copolymers forming dispersed aggregates. A "hydrophilic group", as used herein, refers to a chemical group that promotes solubilization of a molecule containing the group in aqueous solution.

"Hydrophobic polymer segment" refers to a polymer segment which, by itself, is water insoluble. Hydrophobic polymer segments in a copolymer composed of alternating hydrophilic and hydrophobic tend to self-associate or aggregate with other hydrophobic polymer segments when dispersed in an aqueous medium due to interactions between hydrophobic groups and avoidance of the aqueous medium. A "hydrophobic group", as used herein, refers to a chemical group that imparts hydrophobic properties to a hydrophobic monomer by virtue of its presence in the molecule.

"Matrix" refers to a network of polymers suspended in an aqueous medium. Such matrix is composed of a continuous phase of polymer molecules and a liquid dispersed phase of an aqueous medium.

"Pore" refers to an open formation within a matrix through which a molecule can pass and which is filled by an aqueous medium at least when it is unoccupied by a biomolecule.

"Interpolymeric-aggregation transition concentration" refers to the concentration of polymers in a solution at which the viscosity shows a marked rise in viscosity, as a function of polymer concentration.

"Step-reaction polymerization" refers to a polymerization process in which each of a series of chain-growing steps is essentially independent of the preceding step. Step-reaction polymerization includes "condensation polymerization", in which a small molecule such as water is eliminated upon combination of two monomers.

II. Regular, Alternating Copolymers

A polymer matrix of the invention is composed of an aqueous dispersion medium and a matrix of aggregated regular, alternating copolymers. The copolymers form a stable matrix in the solution due to the self-associating of hydrophobic polymer segments in the copolymer. The hydrophilic regions stabilize the particles in the dispersion medium and the hydrophobic regions are attracted to each other because of their repulsion from the aqueous phase and van der Waals forces. Such aggregated copolymers dispersed within an aqueous medium can also be referred to herein as an association colloid, as defined hereinabove. Structures of copolymers formed upon polymerization of hydrophobic and hydrophilic monomers as contemplated by the present invention are described in more detail in the following sections.

A. Copolymer Structures

The basic structures of the regular, alternating copolymers used in the invention are shown in FIGS. 1A–1F. A block copolymer 10 shown in FIG. 1A is composed of regular, alternating hydrophilic polymer segments, such as segment 12, and hydrophobic polymer segments, such as segment 14. In the embodiment shown, each pair of adjacent segments is linked by a bifunctional linking agent 16, as will be discussed below. In another general embodiment, the hydrophilic and hydrophobic polymer segments are linked directly end-to-end, by direct covalent linkage between chemical groups carried on the polymer segment ends, e.g., by amide linkage formed between carboxyl end groups of one type of polymer segment and amine end groups of the second type of polymer segment.

FIG. 1B shows a comb copolymer 18 composed of a series of hydrophilic polymer segments, such as segment 20, which are linked to one another by linkers, such as linker 22, to form a linear backbone 24. A hydrophobic polymer segment, such as segment 26, is attached to each linker.

FIG. 1C shows a tuft copolymer 28 also composed of a series of hydrophilic polymer segments 30, which are linked to one another by linkers, such as linker 32, to form a linear backbone 34. A pair of hydrophobic polymer segment, such as segment 36, 38 are attached to each linker. Alternatively, the linker can be joined at a single attachment site to a central portion of a hydrophobic chain, as described below.

FIG. 1D shows a star copolymer 40 composed of a plurality of hydrophilic polymer segments, such as segment 42, which radiate outwardly from and are attached covalently to a central hub 44. Carried at the end of each hydrophilic polymer is a hydrophobic polymer segment, such as polymer segment 46.

Figure 1F:
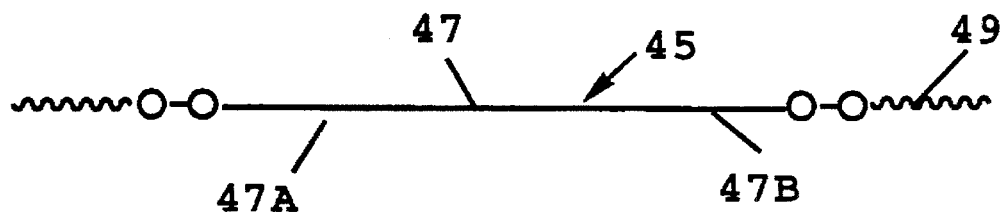

FIGS. 1E and 1F show embodiments of a star copolymer formed of contiguous linear hydrophilic polymer segments having a selected combined length, and a hydrophobic polymer segment carried on each of the free ends of the hydrophilic segments.

In the embodiment shown in FIG. 1E, and indicated at 35, the hydrophilic polymers segments 37, 39 are joined at their adjacent ends by a common anchor 41. Methods for forming such two-arm star polymers are described below. Carried on each free end of the joined hydrophilic polymers is a hydrophobic polymer segments, such as segment 43.

In the embodiment shown in FIG. 1F, and indicated at 45, the hydrophilic polymer segments are formed of a single hydrophilic polymer chain 47; i.e., chain 47 is composed of two polymer segments, 47A and 47B, that are about equal in length. Carried on each free end of the hydrophilic polymer is a hydrophobic polymer segment, such as segment 49.

In each of the copolymers described above, the hydrophilic polymer segments have selected, substantially uniform segment lengths, i.e., the segments are all within a defined, narrow chain-length size. Hydrophilic polymer segments with uniform polymer sizes can be prepared by controlled or step-wise polymerization reactions, or by size separation of a polymer mixture, such as by column chromatography. A variety of hydrophilic polymers, such as polyethyleneglycol, having defined size ranges may be obtained commercially.

In each of the polymer structures, the hydrophobic polymers are carried on and spaced from one another by the hydrophilic polymer segments. In the block, comb, and tuft copolymers shown in FIGS. 1A–1C, the spacing between adjacent hydrophobic polymers (considering the linked hydrophobic polymer in the tuft copolymer as a single segment joined to the hydrophilic polymer in a central region) is just the spacing produced by a single hydrophilic polymer segment. In the star polymer shown in FIGS. 1D–1E, adjacent hydrophobic segments, such as segments 46 and 48, are separated by the spacing produced by two hydrophilic polymer segments.

Monomers used in making hydrophilic polymer segments are preferably functionalized so as to permit ready polymerization with a hydrophobic monomer of the invention, e.g., via condensation. Some preferred hydrophilic monomers for use in the present invention include: linear polyoxides, such as polyethylene oxide also known as polyethyleneglycol (PEG), Carbowax grades and blends thereof, and derivatized PEGs, such as amine derivatives including Jeffamine compounds, linear polyethylene imine, polyacrylic acid, polymethacrylic acid, polyacrylamide, polymethacrylamide, polyvinylalcohol, polyvinylpyrrolidone, polyvinyloxazolidone, water-soluble hydroxyl polymers, such as natural gums (xanthan, dextran, guar, etc.), water-soluble cellulose compounds, such as methylcellulose and hydroxyethylcellulose, and copolymers and blends of these polymers, and the like.

Suitable water-soluble polymers having a wide range of molecular weights (often expressed in terms of solution viscosity, at a given polymer concentration) are available commercially, or can be prepared under defined polymer formation conditions well-known to those skilled in the art (see, generally, M. Morton, *Anionic Polymerization: Principles and Practice,* Academic Press (1983)).

Monomer units used in making hydrophobic polymer segments include alkyl, aryl, and alkaryl groups. Some exemplary monomers used in forming hydrophobic polymer segments include: butyl, pentyl, hexyl, cyclohexyl, phenyl, heptyl, benzyl, octyl, ethylphenyl, nonyl, propylphenyl, decyl, butylphenyl, naphthyl, undecyl, pentylphenyl, dodecyl, hexylphenyl, phenylphenyl, anthracyl, heptylphenyl, lauryl, octylphenyl, nonylphenyl, decylphenyl, undecylphenyl, dodecylphenyl, stearyl, palmityl, and the like, which are commercially available.

Preferably, any of the above-listed hydrophobic groups is present in a copolymer of the invention as a partially or wholly fluorinated hydrocarbon group, as illustrated below. Numerous other hydrophobic groups suitable for use with the present invention will be apparent to the skilled practitioner.

In addition to the hydrophobic and hydrophilic polymer segments, linking groups and star-center groups may be used in construction of the copolymer of the invention. A star-center group, as shown at 40 in FIG. 1D, is a polyfunctional group that permits reaction with a plurality of polymeric chains. Particularly preferred S' anchor groups include ethylene glycol (bi-functional), glycerol (tri-functional), erythritol (four-functional), sorbitol (six-functional), and siloxane (four-functional). It should be apparent from the discussion herein that the alcohol groups of the preferred S' groups listed above can be readily converted to a different functionality, such as isocyanate, without departing from the present invention.

A copolymer of the invention, comprising hydrophobic and hydrophilic groups, linking groups, and any anchor groups generally is macromolecular in size. In particular, the molecular weight of an instant copolymer is preferably from about 4 to about 500 kilodaltons.

B. Synthesis of Copolymers

In the following section, examples of several copolymers, and their synthesis are described, with particular reference to FIGS. 2–8. One preferred hydrophilic polymer segments is PEG. PEG polymers are commercially available in a number of size ranges, or can be synthesized. A number of other hydrophilic polymers may be utilized, such as polyacrylamide, polyvinylalcohol, polyvinylpyrrolidone and water-soluble derivatives of naturally occurring polysaccharides.

Preferred hydrophobic blocks for use in copolymer formulations of the invention include any of a number of alkyl chains, preferably fluorinated alkyl chains 4–20 carbon atoms in length, that have been functionalized at both ends by the same or by different functional groups, such as OH, $NH_2$, aldehyde, or acid groups. In copolymer formulations described below, the preferred hydrophobic blocks are dialcohols or dicarboxylic acids. Alternatively, diamines, dithiols, diesters and dialdehydes could be utilized. It will be appreciated that the specific copolymer formulations and methods of synthesis are only exemplary, and should not be construed to limit the range of polymer formulations applicable to this invention.

Particularly preferred perfluoroalkyl diols for use in forming copolymers of the invention include those having the formula: $(OHCH_2)_2CHCH_2CH_2C_nF_{2n+1}$, where n is preferably 4–14, most preferably, such a diol has n=4–10. Compounds having this formula can be readily prepared by reacting a perfluoroalkyl halide, having the formula $R_f(CH_2)_nCH_2X$ with deprotonated malonate. These perfluoroalkyl halides can be obtained commercially from DuPont, where $R_f$ is a perfluoro group, and X is preferably iodide. The reaction with malonate is followed by reduction of the malonate with $LiAlH_4$.

Another general class of preferred hydrophobic blocks for use in copolymer formulations of the invention include alkyl chains, preferably fluorinated alkyl chains 4–20 carbon atoms in length, that have been functionalized at one end by a functional group such as described above. Particularly preferred perfluoroalkyl chains in this aspect of the invention include those having the formula: $C_nF_{2n+1}CH_2CH_2OH$, where n is preferably 4–14, and more preferably, 7–12. Compounds having the formula $C_nF_{2n+1}CH_2OH$, are similarly suitable. Compounds of these types can be obtained from commercial sources or can be prepared by known methods.

1. Block Copolymers

The hydrophilic block and the hydrophobic block may be coupled to each other by a bifunctional linking reagents, or directly end to end. In one general embodiment, the hydrophilic and hydrophobic polymers both contain the same chemical-group termini, such as OH groups. Here the coupling reagent is a bifunctional reagent which is reactive toward the terminal chemical groups of one of the two polymer segments under one set of reaction conditions, to activate the polymer ends, and is reactive toward the same terminal groups under a second set of reaction conditions, to couple the hydrophilic and hydrophobic polymers end to end.

Figure 2:
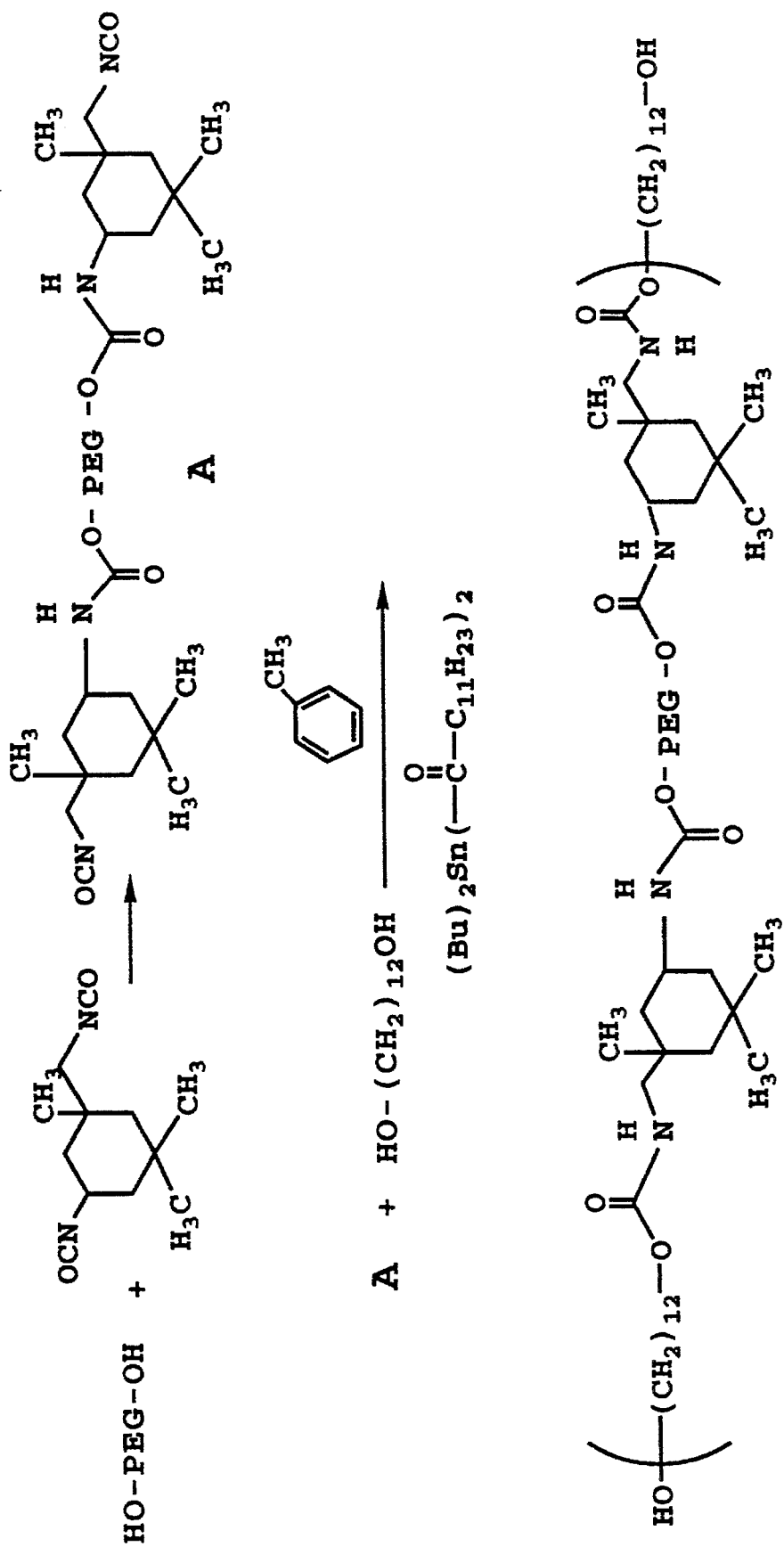
FIG. 2 illustrates a synthetic scheme for forming a block copolymer composed of regular alternating polyethylene glycol (PEG) and hydrocarbon segments which are linked by a diisocyanate compound.

This approach is illustrated by the reaction scheme illustrated in FIG. 2, where the bifunctional reagent is isophorone diisocyanate. This reagent contains two isocyanate linkages with distinct reactivities towards free hydroxyl groups. Thus the reagent allows for an activation reaction involving one of the two reactive CNO groups in the reagent, for activation of reactive end groups in one of the block copolymer segments, and subsequent reaction with the other block polymer, to complete copolymer synthesis by coupling activated ends of the hydrophilic polymer segments to the ends of hydrophobic segments.

In the reaction method illustrated in FIG. 2, a PEG polymer segment is reacted with isophorone diisocyanate, under conditions which activate the PEG OH ends as shown (by reaction with the more reactive ring —NCO group of isophorone diisocyanate). Other asymmetric diisocyanates which can be employed in this general reaction scheme are 2,2,4-trimethyl-1,6-diisocyanatohexane and 4-chloro-1,3-phenylene diisocyanate.

The reaction conditions are selected to minimize reaction with the less reactive $CH_2$-NCO group. The terminal isocyanate groups are then converted to the respective urethane groups by reaction with dodecane-1,12-diol in toluene containing dibutyl tin dilaurate, forming the desired block copolymer, as shown at the bottom in FIG. 2.

Alternatively, the activated ends of hydrophobic polymer segments can be coupled to the ends of hydrophilic polymer segments, essentially by reversing the order of the activation and copolymer coupling reactions shown in FIG. 2. Here a hydrophobic polymer segment, such as a fluorinated polymer segment, is first activated with a suitable diisocyanate, and the activated polymer segments is then reacted with PEG polymer segments to complete copolymer synthesis.

In a related method, the diisocyanate of a suitable hydrophobic polymer segment is formed, and then reacted with the hydrophilic polymer segments under suitable condensation reaction conditions. Preferred fluorocarbon diisocyanates suitable for preparing a block copolymer of the present invention are alpha,omega-diisocyanate perfluoroalkanes with two intervening methylene groups. These compounds have the general formula $OCNCH_2CH_2(CF_2)_nCH_2CH_2NCO$, where n is an even number. These fluorocarbon diisocyanates can be readily prepared by published methods (Malik).

In another general method for forming a block copolymer of the type described, the hydrophilic polymer segments have one type of terminal chemical groups, such as acid groups, and the hydrophobic polymer segments have a second type of terminal chemical groups, such as amine groups. The two polymers are then joined end-to-end in alternating sequence by direct coupling of their ends, i.e., through an amide linkage, or using a bifunctional reagent capable of joining the two different types of chemical groups.

Figure 3:
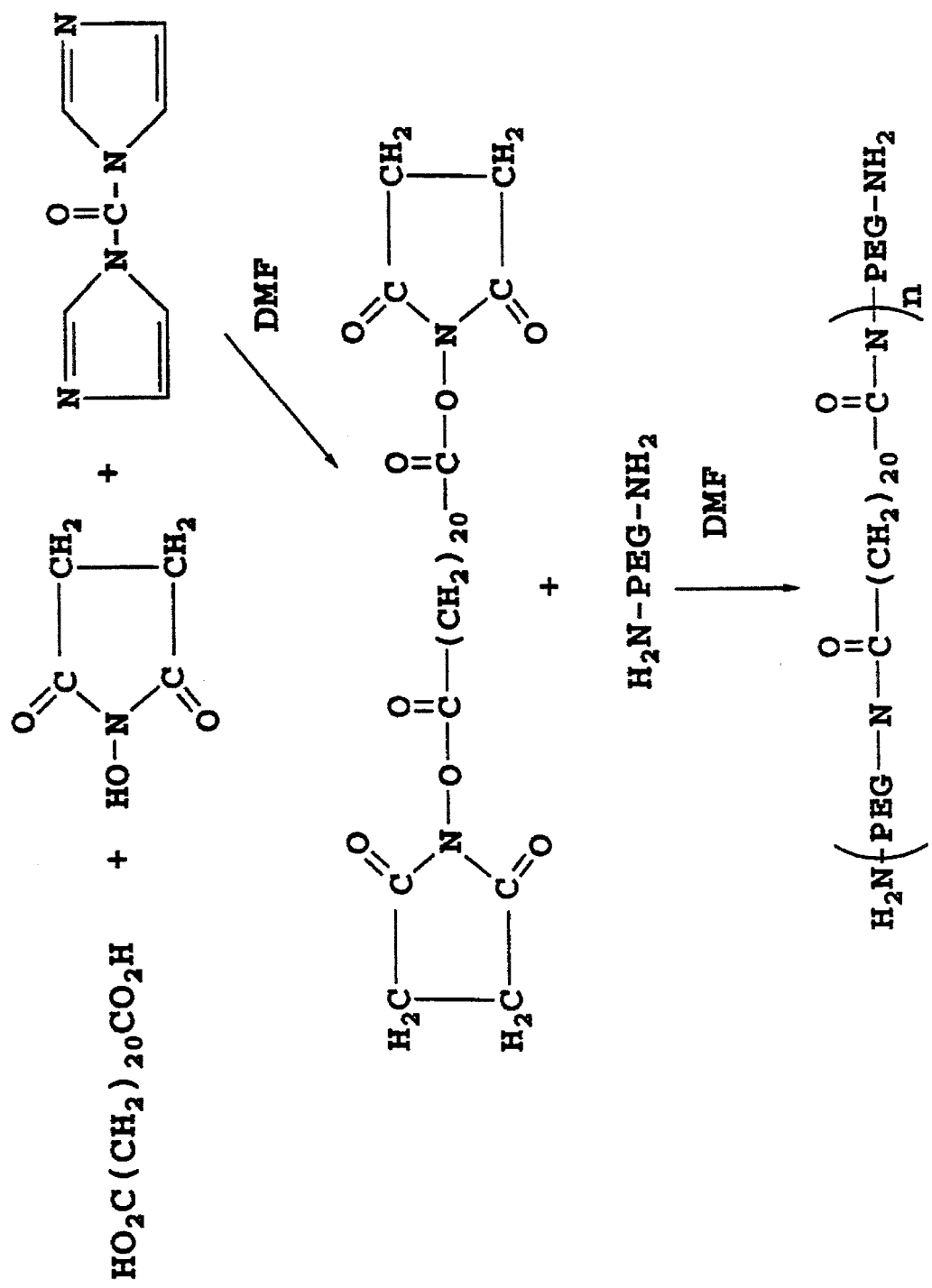
FIG. 3 illustrates another synthetic scheme for forming a block copolymer composed of regular alternating PEG, and hydrocarbon segments linked through amide linkages.

This general method is illustrated in FIG. 3 for the synthesis of a block copolymer composed of alternating segments of PEG bis (amine) and docosanedioic acid. To prepare this copolymer, the terminal carboxylic acid groups of PEG dicarboxylic acid are activated by reaction with N-hydroxysuccinimide in the presence of dicyclohexylcarbodiimide (DCCD) in dimethylformamide (DMF). The resulting docosanedioate ester, terminally linked by N-succinimide, is reacted with a PEG diamine. The resulting product contains alternating hydrophilic PEG polymer blocks and the hydrophobic C20 blocks coupled through amide linkages.

2. Comb Copolymers

The general methods outlined above for the synthesis of block copolymers are also suitable for making comb copolymers, where the hydrophobic segments used in the synthesis of the comb copolymers include short backbone linkers whose termini have suitable chemical groups, such as hydroxyl, amine or carboxyl groups, and which carry a hydrophobic polymer segment (or a chemical group by which a hydrophobic polymer segment can be covalently coupled) between its two termini.

Figure 4:
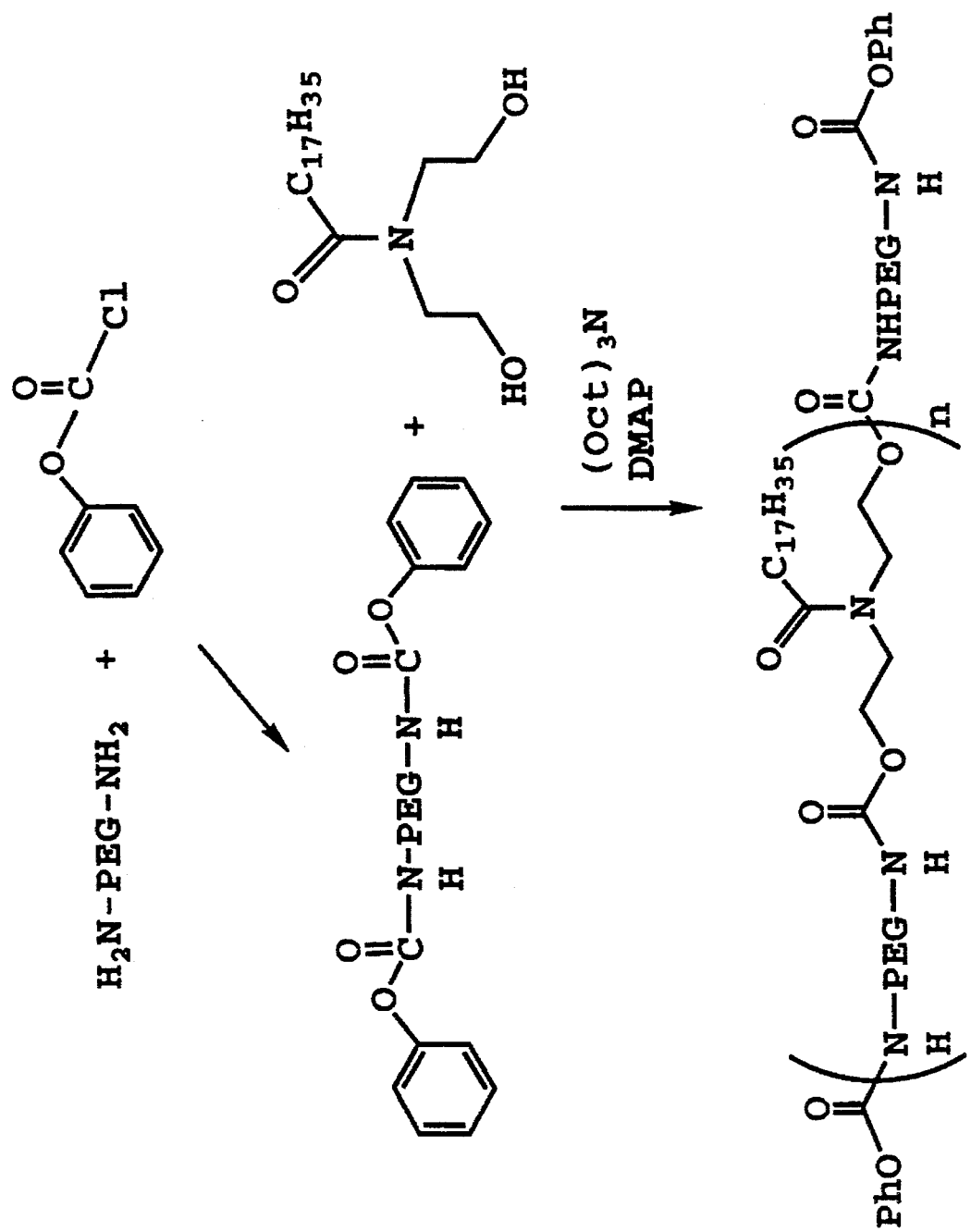
FIG. 4 illustrates a synthetic scheme for forming a comb block copolymer of regular alternating segments of a polyethylene glycol bis (amine) and hydrocarbon segments coupled by urethane linkages.

This general approach is illustrated in FIG. 4 for the synthesis of comb copolymer formed of PEG bis (amine) hydrophilic segments and a bis-N,N-(2-hydroxyethyl)amide of a fatty acid hydrophobic segment. As a first step, the polyethylene glycol bis (amine) is reacted with benzyl chloroformate to form the activated polyethylene glycol bisurethane. The activated PEG is subsequently converted by thermal elimination in the presence of trioctylamine, to its bisisocyanate, and this product is then reacted with a hydrocarbon diol in the presence of dimethylaminopyridine as copolymerization catalysts. The resulting product contains alternating hydrophilic PEG polymer blocks and hydrophobic fatty acid comb blocks coupled by urethane linkages. Details of the copolymer synthesis reaction are given in Example 1.

Figure 5:
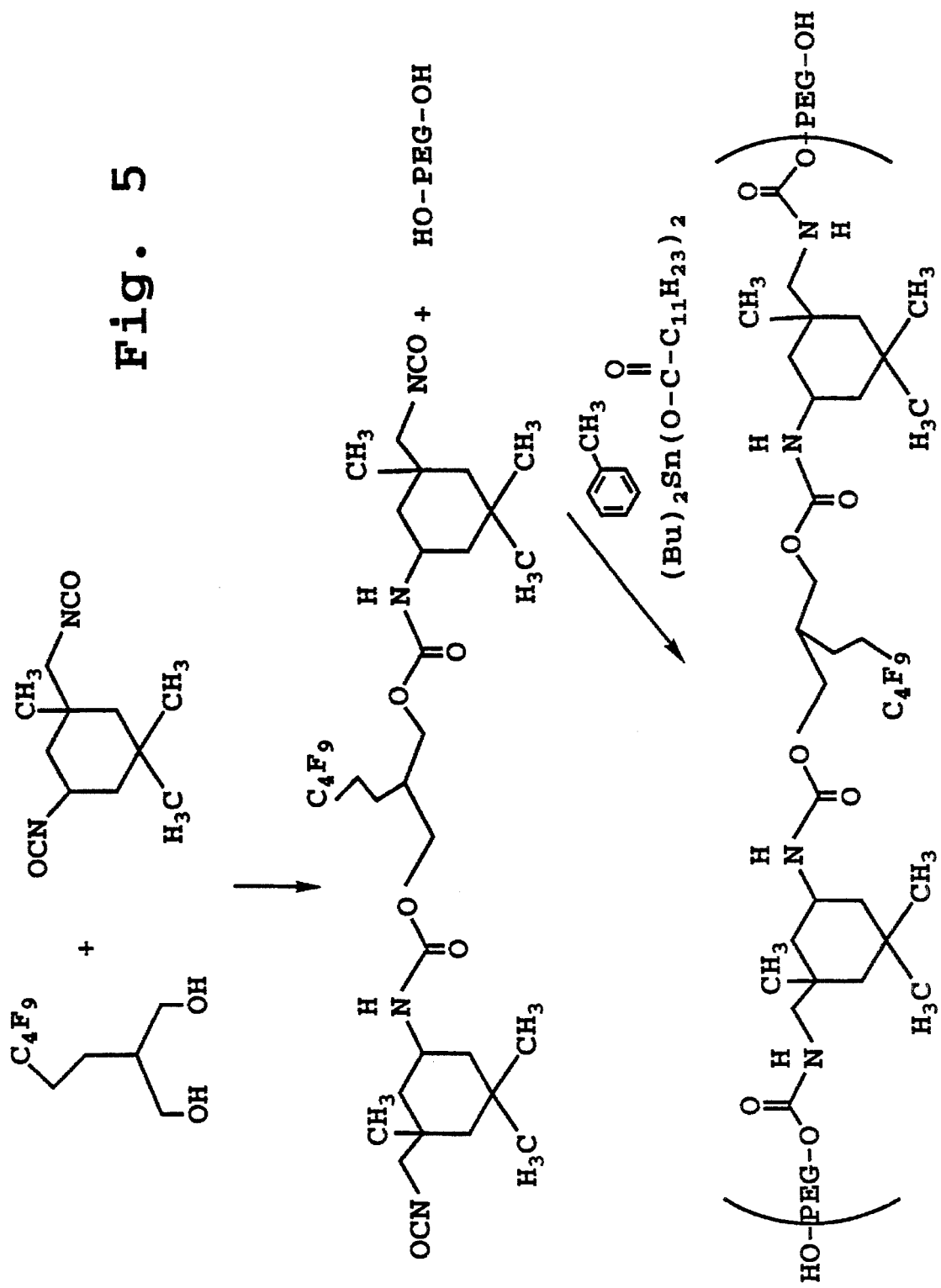
FIG. 5 illustrates a synthetic scheme for forming a comb block copolymer of regular alternating segments of PEG and polyfluorinated hydrocarbon segments which are linked by a diisocyanate compound.

A reaction scheme analogous to the scheme illustrated in FIG. 2, employing an isophorone diisocyanate coupling agent, is shown in FIG. 5. Here the OH termini a fluorohydrocarbon derivative of propane-1,3-diol, 2-(C4F9C2H4)propane-1,3-diol (C4F9 diol) are activated with isophorone diisocyanate, under conditions which are selective for OH activation by the ring —NCO group of the isocyanate. The C4F9 diol is synthesized by treating diethyl malonate with base in the presence of the iodide of the fluorohydrocarbon of choice, in this case C4F9C2H4I. Subsequently, the diester groups of the derivatized diethyl malonate are reduced by lithium aluminum hydride. Reaction procedures for the synthesis of the C4F9 diol are detailed in U.S. Pat. No. 3,504,016. Details of the activation reaction are given in Example 2.

The terminal isocyanate groups in the activated compound are then converted to the respective urethane groups by reaction with PEG in toluene containing dibutyl tin dilaurate, forming the desired block copolymer, as shown at the bottom in FIG. 5. The resulting product contains alternating hydrophilic PEG polymer blocks and hydrophobic blocks coupled by isophorone bisurethane linkages. Each hydrophobic block contains a fluorohydrocarbon chain in a comb configuration.

Example 3 describes a reaction used in forming a comb copolymer with a PEG (MW 3350, Carbowax 3350™) polymer segment. Examples 4, 5, and 6 describe similar methods for forming a comb copolymer having PEG segments of MW 4600 daltons (Example 4), 1400 daltons (Example 5), and 15,000 daltons (Example 7).

Figure 6:
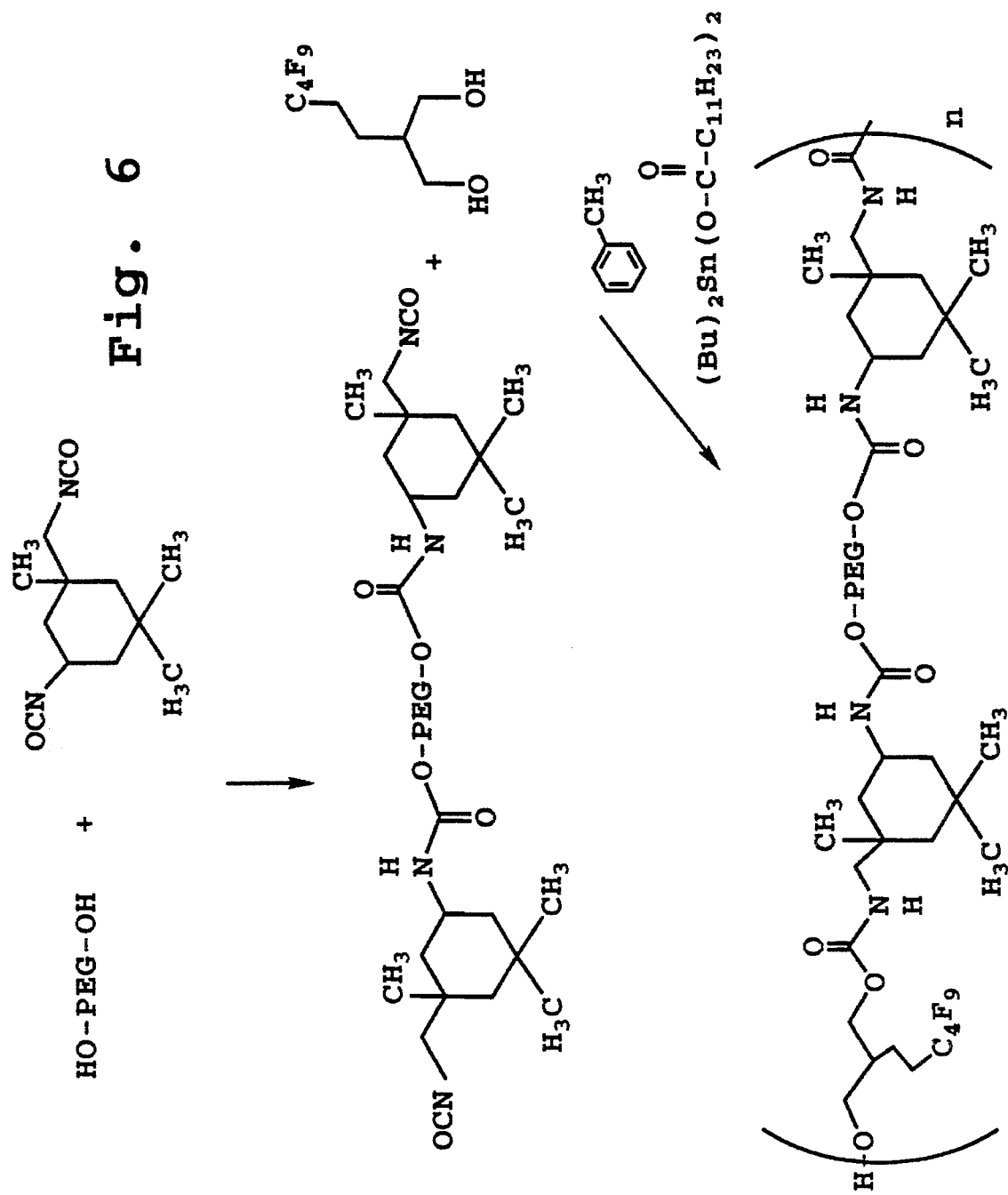
FIG. 6 illustrates a synthetic scheme for forming another comb copolymer of regular alternating segments of PEG and polyfluorinated hydrocarbon segments which are linked by a diisocyanate compound.

FIG. 6 illustrates a similar method of forming a comb copolymer, but where the order of activation and copolymer coupling steps has been reversed. In the method shown, PEG is first activated with isoperone diisocyanate, to form activated PRE polymer segments, similar to the method described with respect to FIG. 2. The activated PEG segments are then reacted with the diol-linker hydrocarbon polymer, such as the above fluorohydrocarbon derivative of propane-1,3-diol, 2-(C4F9C2H4)propane-1,3-diol (C4F9 diol), to complete copolymer synthesis. Details of this synthesis are given in Examples 13 and 14.

3. Tuft Copolymers

In the tuft copolymer configuration, the linking moieties between adjacent hydrophilic polymers carry two or more hydrophobic polymer segments, which thus radiate from sites, typically backbone linkers, which are evenly spaced along the hydrophilic backbone of the polymer. Three general methods of synthesizing such polymers will be described. The first involves building a hydrophilic polymer backbone composed of hydrophilic polymer segments joined by backbone linkers which provide two or more chemical groups at which hydrophobic polymers can be attached.

Figure 7:
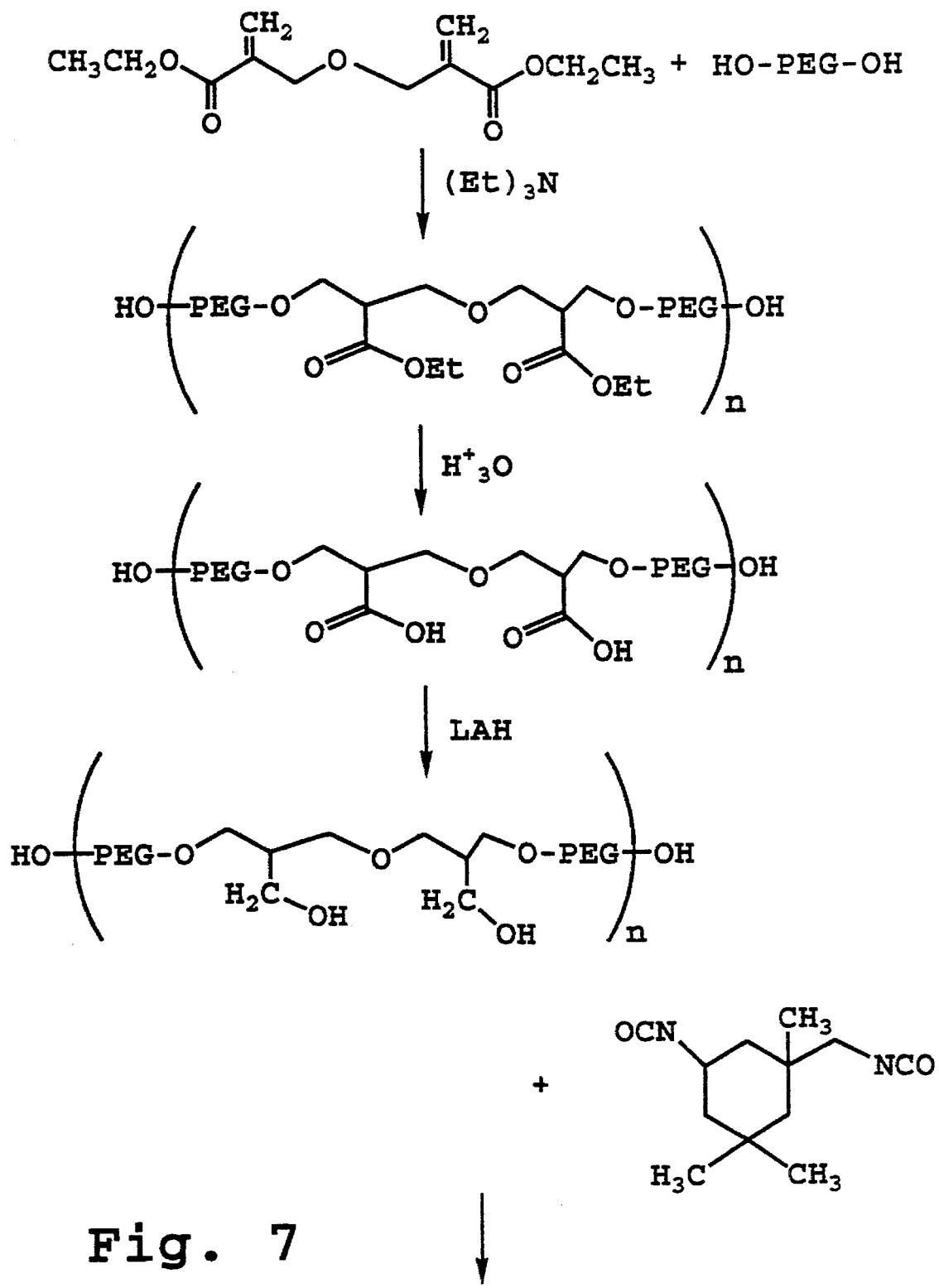
FIG. 7 illustrates a synthetic scheme for forming a tuft copolymer of regular alternating segments of polyethylene glycol, and polyfluorinated hydrocarbon segments.

This general approach is illustrated in FIG. 7. The synthetic method shown involves the Michael addition of 2 dialcohols, such as PEG polymer segments, to ethyl bisacrylate monoether. The reaction is carried out in triethylamine and, after LAH reduction of the ester, forms a hydrophilic polymer having, at evenly spaced intervals therealong (corresponding to the spacing between adjacent PEG segments), linking groups with a two free hydroxyl groups.

The next step entails the activation of the free hydroxyl groups, including the two terminal 0H groups, and the free linker OH groups, by isophorone diisocyanate, as shown, under conditions which selectively activate, but do not crosslink the free hydroxyl groups. The activated isocyanate groups along the polymer chain are now converted to the respective urethane groups by reaction with the alcohol of the fluorohydrocarbon in the presence of toluene and dibutyl tin dilaurate. The resulting product contains alternating hydrophilic blocks and hydrophobic blocks linked by isophorone bisurethane linkage groups. Each hydrophobic group contains two fluorohydrocarbon chains in a tuft configuration.

In a second, related method, the linkers used is coupling the hydrophobic chain are prepared to include the two or more hydrophobic chains prior to coupling the hydrophilic polymer chains.

In a third general method, the hydrophobic chains are themselves used in coupling the hydrophilic polymer segments. As one example, a hydrocarbon chain with a single internal double bond is oxidized, e.g., by treatment with permanganate or osmium tetroxide, to produce a diol across the double bond. The diol is then reacted with activated PEG, e.g., PEG first activated with isopherone diioscyanate. The polymer segment-coupling reaction is carried out under conditions which couple PEG termini to the free OH groups of the hydrophobic chain diol. The resulting copolymer contains segments of PEG coupled through aliphatic chains, with end regions of the aliphatic chain serving as the hydrophobic polymer segments.

4. Star Copolymers

A star copolymer formed in accordance with the invention can be made by providing a suitable star-center molecule which can be derivatized with multiple (two of more) hydrophilic polymer segments. Suitable star-center molecules include, for example, ethylene glycol, providing two OH groups, glycerol, providing three OH groups, erythritol, providing four hydroxyl groups, and various mono and oligosaccharides, providing five or more free OH groups.

The various reaction methods described above, or other suitable coupling methods, can be used for coupling hydrophilic polymer segments to the star-center molecule. In the method illustrated in FIG. 8A, erythritol is reacted with succinate to generate four terminal carboxylic acid groups. The carboxylic acid derivatives are activated by N-hydroxysuccinimide and DCCD for reaction with four polyethylene glycol bis (amine)s, forming the 4-PEG-NH$_2$ star polymer shown at the bottom of FIG. 8A.

Figure 8A:
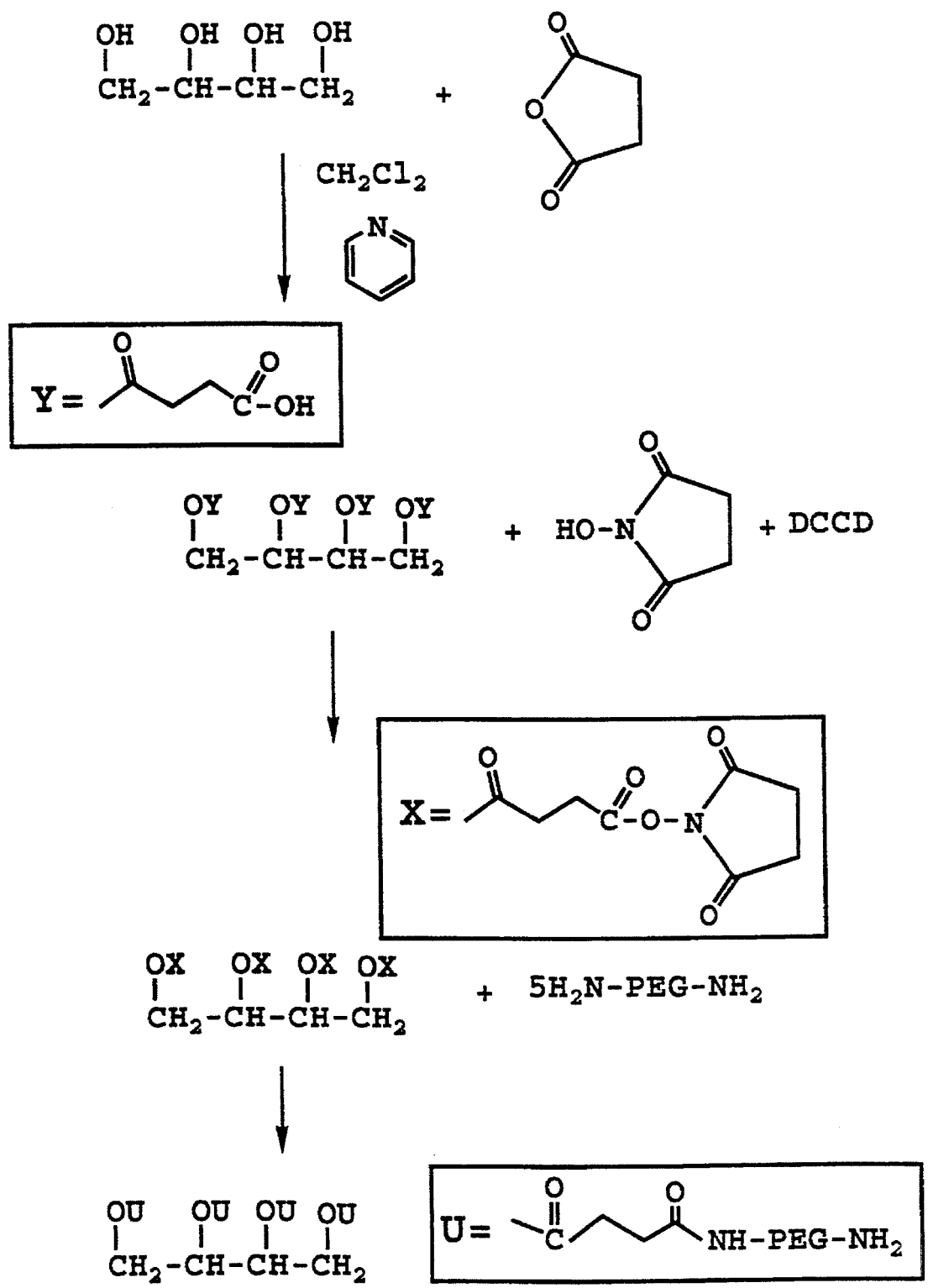
FIGS. 8A and 8B illustrate synthetic methods for forming a star copolymer of PEG (FIG. 8A), and for derivatizing the ends of the PEG polymers with polyfluorinated hydrocarbon segments via amide and urethane linkages (FIG. 8B)
Figure 8B:
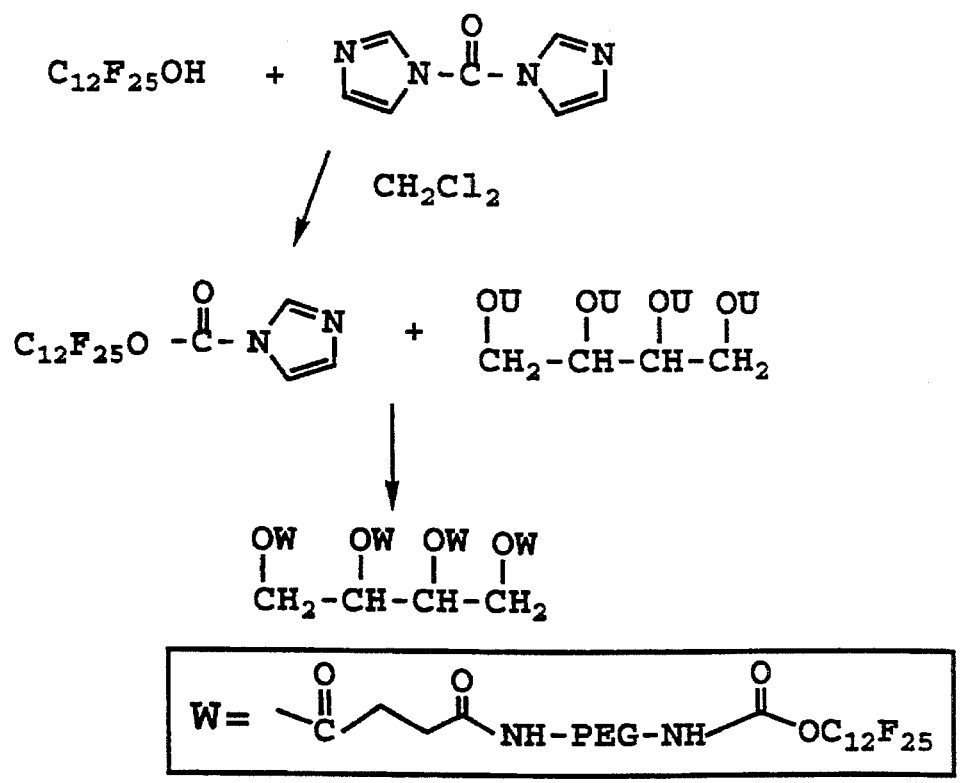

The reaction for joining fluorocarbon polymer chains to the PEG-NH$_2$ star polymer is illustrated in FIG. 8B. As seen, the alcohol of a fluorohydrocarbon is activated by reaction with carbonyl diimidazole and the activated fluorohydrocarbon is then reacted with the terminal amine groups of the star-like structure. The resulting product has a star-like configuration which contains a base (common anchor) to which are attached multiple hydrophilic PEG blocks. To these hydrophilic blocks are attached linear hydrophobic blocks by amide linkages. Each hydrophobic block is preferably a fluorohydrocarbon chain.

Some preferred fluorocarbon monools include the BA-L, BA, and BA-N fluoroalcohols of DuPont sold under the ZONYL brand name. These products are actually mixtures of fluoroalcohols having the general formula R$_f$CH$_2$CH$_2$OH. The R$_f$ fluoroalkyl chain has one of the following perfluoro aliphatic formulas: $C_4F_9$, $C_6F_{13}$, $C_8F_{17}$, $C_{10}F_{21}$, $C_{12}F_{25}$, $C_{14}F_{29}$, or higher. Pure fractions of these mixtures can be readily obtained by fractional distillation.

In another embodiment, the copolymer is formed of contiguous linear hydrophilic segments having a selected combined length, and a hydrophobic polymer segment carried on each of the free ends of the hydrophilic segments, as illustrated in FIGS. 1E and 1F.

In one approach, the linear hydrophilic segments are formed of two hydrophilic segments which are joined at their adjacent ends by a common anchor (FIG. 1E). A copolymer having this type of structure can be prepared by modification of the scheme illustrated in FIGS. 8A and 8B, where a diol such as ethylene glycol (HOCH$_2$CH$_2$OH) is used instead of erythritol; the resultant copolymer is composed of two hydrophilic segments which are joined at their adjacent ends by a common anchor, and a hydrophobic polymer segment carried on each of the free ends of the hydrophilic segments. Other coupling methods, such as described above, may also be used.

In a second approach, the linear hydrophilic segments are formed of (from) a single linear polymer chain, as illustrated in FIG. 1F. Copolymers of this type may be conveniently prepared by reacting the activated ends of a linear hydrophilic polymer chain of defined length with a suitably reactive hydrophobic compound, to attach a hydrophobic segment to each free end of the hydrophilic chain.

The approach is illustrated by the synthetic methods employed in Examples 16–21, where the hydrophilic polymer chain is a PEG chain of defined length. With reference to Example 16, anhydrous PEG (35,000 MW) is reacted with isophorone diisocyanate to form an activated diol (activated alcohol) having the structure shown at structure A in FIG. 2. The activated diol is then reacted with $C_6F_{13}CH_2CH_2OH$ to form a star copolymer represented by the formula PEG-35,000-$(C_6F_{13})_2$, having a fluorocarbon hydrophobic segment attached at each end. Syntheses of star copolymers containing other hydrophobic and hydrophilic segments are given in Example 17–21.

It will be appreciated that the spacing between hydrophobic regions can be controlled by using a hydrophilic polymer chain of defined length. It will also be appreciated from the methods discussed above that other coupling schemes may be used to prepare these types of copolymers.

III. Copolymer Matrix

A copolymer of the invention can be dispersed in an aqueous medium to form a medium suitable for electrophoretic separation of biopolymers, e.g., peptides, nucleic acids, and polysaccharides. A medium formed upon dispersion of the copolymer of the invention in an aqueous medium is said to be a "matrix" formed by aggregated copolymers.

When the copolymer is dispersed in an aqueous medium to form a polymer matrix, the copolymer molecules of the matrix form macromolecular aggregates, primarily due to associations between the hydrophobic portions of individual copolymer molecules within the medium. A polymer matrix so formed can be present as what is conventionally termed an "association colloid", as defined hereinbefore. Structures dispersed in the aqueous medium and characterized above as being "aggregates" may be "micelles" or "micellar" in nature, since they share a property common to micelles found in other contexts, namely, they have a hydrophobic interior and and a hydrophilic exterior shell that interacts with the surrounding medium.

According to an important feature of the invention, it has been discovered that the regular, alternating copolymers described above form a polymer matrix having a relatively uniform mesh size, as evidenced by the ability of the medium to effect a high-resolution separation of biomolecules in a defined molecular size range. The uniform mesh size is presumably related to the regular (i.e., substantially uniform) spacing between adjacent hydrophobic polymer segments, provided by the substantially uniform-size hydrophilic polymer segments connecting the hydrophobic polymers.

Figure 9:
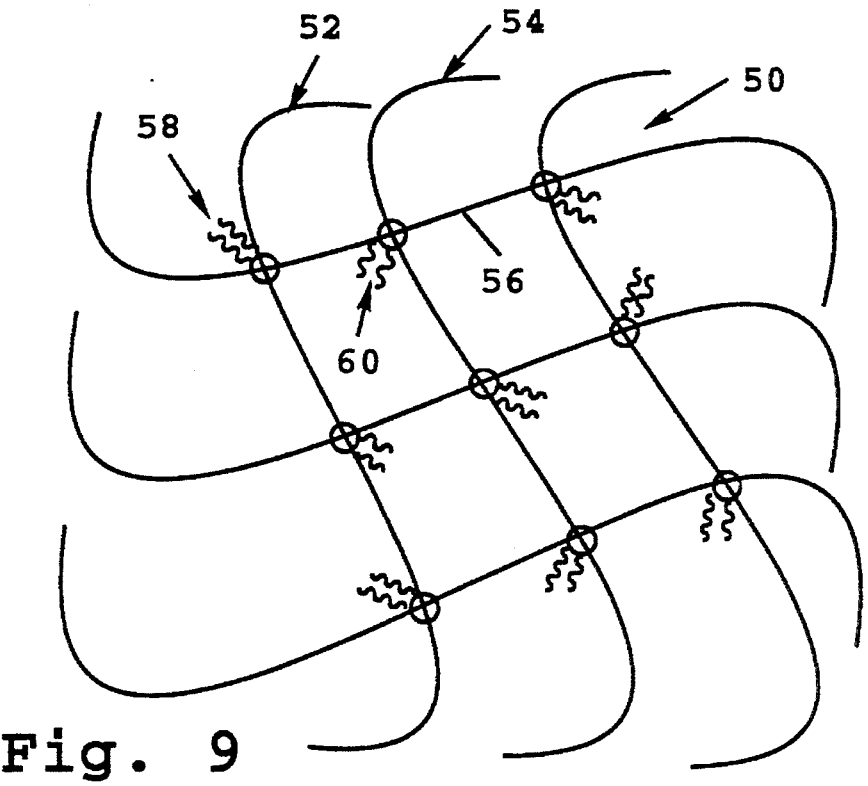
FIG. 9 is a representation, in two-dimensions, of a copolymer matrix formed in accordance with the invention.

FIG. 9 shows, in idealized form, a 2-dimensional portion of a matrix 50 having a uniform mesh size. The mesh shown here is formed by comb copolymers, such as copolymers 52, 54, 56, each formed of hydrophilic polymer segments (smooth lines) spaced from one another by hydrophobic segments (wavy lines). As seen, the polymers are joined to one another by aggregates of hydrophobic polymer segments, such as the aggregate of two such segments indicated at 58 and 60 between polymers 52, 56, and 54, 56 respectively. It can be appreciated that the spacing between adjacent aggregates is directly related to the length of the hydrophilic polymer segments separating adjacent hydrophobic polymer, with longer hydrophilic polymer segments giving rise to a greater mesh size.

In forming the matrix medium, copolymer is added to a final concentration which is above the interpolymeric-aggregation transition concentration of the polymer. This concentration can be determined conventionally from a viscosity/concentration plot. The critical concentration is the copolymer concentration at which viscosity increases markedly, as a function of increasing copolymer concentration.

To form the copolymer matrix from prepolymerized material, a copolymer can be added in powder form to a given volume of aqueous medium and the copolymer allowed to disperse under selected mixing conditions, for example with vortexing. Typically, the copolymer mixture is allowed to sit for several hours after mixing to ensure complete dissolution of the polymer.

Additional aqueous medium can be added to the mixture to reduce viscosity, or additional polymer can be added or the matrix can be dehydrated, e.g., under reduced pressure, in order to increase viscosity. Such a matrix is characterized as having a substantially homogeneous composition, which composition comprises the copolymers and the aqueous medium, including any buffers, electrolytes, metal ion chelating agents, and the like.

The copolymer matrix can be formed in an aqueous electrolyte medium, such as a conventional electrophoresis buffer. The electrolyte medium can be formulated to include water-miscible solvents, such as DMSO, ethanol, and the like, if desired to increase the solubility of certain molecular species in the matrix. Additionally, the electrolyte medium can include buffer components, preferably at a 10–150 mM concentration; salts, typically at a 50–120 mM concentration; as well as a heavy metal ion chelator, such as EDTA. Also, the solution can contain a denaturant, such as urea, which functions to minimize interactions between biomolecules and between the biomolecules and the walls of a matrix support. The solution can also include an intercalating agent, such as ethidium bromide, if desired to increase separation efficiencies of duplex DNAs.

The copolymer matrix can also be employed in isoelectric focusing (IEF) procedures, as are wellknown. The matrix used in such an IEF procedure is prepared to include standard ampholyte species that form a selected pH gradient upon equilibration in an electric field.

As noted above, the matrix medium of the invention has a substantially uniform mesh size range that permits electrophoretic separation of biopolymer molecules in a defined molecular size range. According to another important feature of the invention, it has been found that the effective mesh of the matrix can be systematically controlled, for separating different size range of biomolecules electrophoretically, by selectively varying the chain size of the hydrophilic polymer segments used in forming the copolymers.

When a polymer of the invention comprises copolymers have a comb structure, as defined above, the spacing between the hydrophobic chains along the backbone is preferably between about 50 and 1,000 backbone chain atoms. For fractionating DNA fragments in size ranges of less than about 100 basepairs, a backbone spacing (length of hydrophilic polymer segment) of about 100 chain atoms is preferred. When DNA molecules (double-stranded) greater than about 1,000 basepairs in length are to be fractionated, a backbone spacing between about 500–1,000 chain atoms is preferred. When single-stranded DNAs having lengths of between about 100–1,000 basepairs are to be separated, a backbone spacing between about 100–800 chain atoms is preferred. It will be understood for the purposes of this paragraph that "basepairs" means "basepairs" for double-stranded fragments and "bases" for single-stranded fragments.

IV. Electrophoresis System

In another aspect, the invention includes an electrophoresis system for separating biopolymers in a given size or molecular weight range. The system includes a support which defines an elongate channel connectable at opposite ends to opposing polarity terminal of a voltage source, and contained with the channel, an electrophoresis medium of the type described in Section III above.

A number of preparative-scale chambers, e.g., tubes, in a variety of diameters and lengths are available for use as a support in the invention. Typically, diameters of about 2–10 mm, and lengths of between about 15–40 cm are employed for preparative scale fractionation. Flow of matrix material can be restricted by the use of a frit or constricted plug or the like which prevents flow of the viscoelastic material out of the chamber. Alternatively, or in addition, at high viscosities in the range 200 psi or greater pumping pressure, the matrix is relatively stable against flow under gravity during the period of electrophoresis.

The matrix support is prepared by pumping the polymer material into the separation chamber to fill the chamber substantially uniformly and form the separation matrix. The matrix support defines an elongate separation chamber, which may be filled at one end region of the chamber with a buffer or electrolyte solution in addition to an instant copolymer matrix.

A pumping system is loaded with a copolymer matrix, and a pump is set to a selected pumping speed, typically 50–100 μl/min. The material is pumped into the chamber until the chamber is filled to a desired level.

When pumped into the chamber, the matrix material fills the chamber substantially uniformly and homogeneously, by which is meant the polymer matrix in the chamber has a substantially uniform density throughout the chamber substantially without discontinuities or voids in the matrix. This feature of the invention is achieved by virtue of: (a) the uniform density and homogeneous bulk properties of the matrix which are achievable by forming the matrix outside of the tube, (b) the ability to pump the matrix into the tube without breaks, cracks, bubbles or voids forming in the matrix, and (c) the ability of the matrix to completely fill the chamber space as it is pumped into the tube with concurrent displacement of any material, e.g., gas, in the chamber.

V. Method of Fractionating Biopolymers

Figure 10:
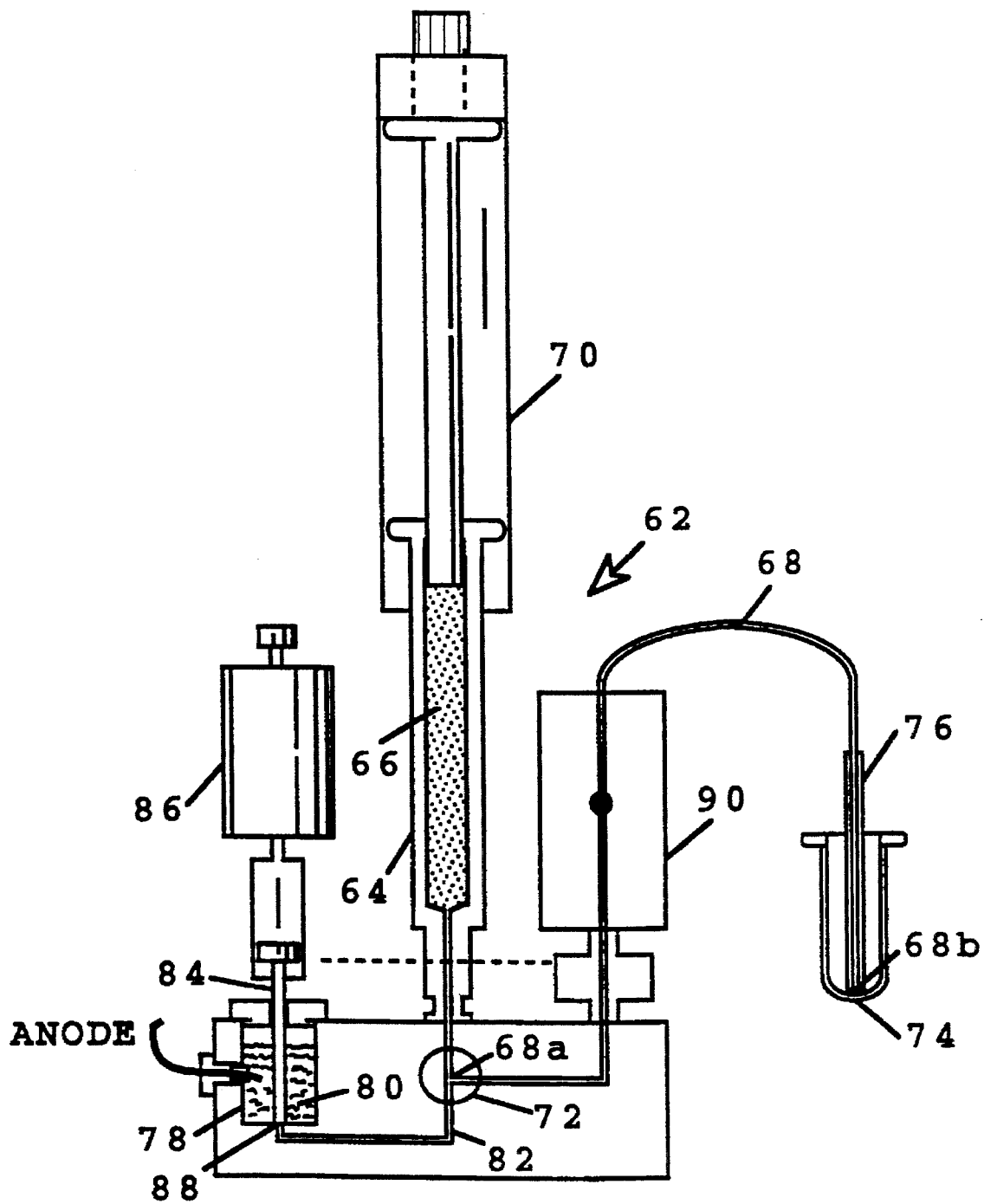
FIG. 10 illustrates a capillary gel electrophoresis apparatus used in the invention.

Also contemplated is an apparatus and associated system for fractionating macromolecules by electrophoresis or isoelectric focusing. FIG. 10 shows the basic elements of an electrophoresis apparatus 62 for use in the method. The apparatus includes a syringe 64 which is filled with the copolymer matrix medium of the invention, here indicated at 66, and a CE tube 68 having an anode end 68a and a cathode end 68b. Copolymer matrix solution is introduced into the tube, through its anode end, via a valve 72 connecting the syringe to the tube, as indicated. Pumping pressure for filling the tube with the matrix medium is provided by a piston type actuator 70 which acts on the syringe plunger, as indicated. The actuator is typically designed to exert a pumping pressure of between about 100–500 psi.

CE tube 68 is preferably a fused silica capillary tube with a polyimide coating. One preferred tubing has a 375 micron outer diameter and a selected inner diameter between 50–150 microns, such as is available from Polymicro Technologies (Phoenix, Ariz.).

A sample reservoir 74 in the apparatus contains the macromolecular mixture, e.g., nucleic acid fragments, which is to be loaded into one end of the tube. Preferably the sample material is dissolved in an electrolytic solution or in water. The sample reservoirs may be carried on a carousel or the like, for placement at a position in which the lower end of the tube can be immersed in the reservoir fluid. The carousel may carry additional reservoirs containing solutions for cleaning and flushing the tube between electrophoretic runs. The cathodic end of tube 68 includes an electrode having a metal tip which extends into the cathodic buffer solution during electrophoresis.

The opposite, anodic end of the tube communicates with an anodic reservoir 78 and is immersed in an anodic electrolyte solution 80 contained in the reservoir. An ion-flow tube 82 connects the reservoir buffer with the anodic end of tube 68 through valve 72. A second tube 84 in the reservoir is connected to a vacuum system 86 for drawing fluid, e.g., washing and cleaning solutions, and electrophoresis polymer solution, through the tube. Loading the nucleic acid sample material in the reservoir into the tube is by electrokinetic injection. Liquid flow through the lower end of tube 84 is controlled by a solenoid activated needle valve 88.

A high voltage supply (not shown) in the apparatus is connected to the cathodic and anodic reservoirs for applying a selected electric potential between the two reservoirs. The power supply leads are connected to platinum electrodes in the cathodic and anodic reservoirs, respectively. The power supply may be designed for applying a constant voltage (DC) across the electrodes, preferably at a voltage setting of between 5–50 KV. Alternatively, or in addition, the power supply may be designed to apply a selected-frequency, pulsed voltage between the reservoirs. In general, the shorter the capillary tube, the higher the electric field strength that can be applied, and the more rapid the electrophoretic separation. When operated in a pulsed voltage mode, the power supply preferably outputs a square wave pulse at an adjustable frequency of about 0.01 Hz up to the kHertz range. Higher pulse frequencies, even into the MHz range may be suitable for some applications.

Completing the description of the system, a detector in the system 90 is positioned adjacent the anodic end of the tube, for optically monitoring nucleic acid fragments migrating through an optical detection zone in the tube. The detector may be designed either for UV absorption detection and/or for fluorescence emission detection. UV absorbance is typically carried out at 240–280 nm, using, for example, a Kratos 783 UV absorbance detector, which has been modified by Applied Biosystems (Foster City, Calif.) by replacing the flow cell with a capillary holder. Fluorescence emission detection is preferably carried out at a selected excitation wavelength which is adjustable between about 240–600 nm depending on the fluorescent species associated with the nucleic acid fragments. One exemplary fluorescence detector is an HP1046A detector available from Hewlett-Packard (Palo Alto, Calif.), and modified as above for capillary tube detection. The detector can be connected to an integrator/ plotter for recording electrophoretic peaks.

In operation, a capillary tube is thoroughly washed by drawing suitable cleaning and rinsing solutions through the tube by applying a vacuum to an anodic reservoir. The tube is then flushed with several volumes of the electrolytic copolymer matrix solution, and the sample is electrokinetically injected into the cathodic tube end. A voltage is applied between the cathodic and anodic reservoirs until all of the fragment peaks have passed through the detection zone.

It will also be appreciated that the electrophoresis system can be readily adapted for collecting nucleic acid fragments for preparative electrophoresis applications. Sample collection may be accomplished, for example, by providing a series of cathodic reservoirs into which the fragments can be eluted.

A separated fraction of biopolymers can be withdrawn from a matrix containing the molecules by a number of methods. The biopolymers can be withdrawn by eluting the matrix with an aqueous medium in which the biopolymers are soluble. Preferably, the elution medium is buffered with an electrolyte that increases the solubility of the biopolymer in the medium.

Fractionated molecules can also be separated from one of the copolymer matrices described above by exposing the molecules to well-known electrophoresis conditions whereby the molecules are drawn from the matrix into a solvent, e.g., an aqueous medium. The electrophoresis conditions can be augmented with sonication to facilitate removal of the molecules from the matrix.

The fractionation method of the invention finds utility in any of a variety of applications requiring size fractionation of single-stranded or duplex nucleic acids. These applications include electrophoretic separations for restriction analysis, including analysis of restriction fragment length polymorphisms for genetic screening, confirming vector construction, identifying specific nucleic acid fragments on the basis of size and/or hybridization to nucleic acid probes, and fractionating single-stranded fragments for chemical or enzymatic sequencing.

Figure 11:
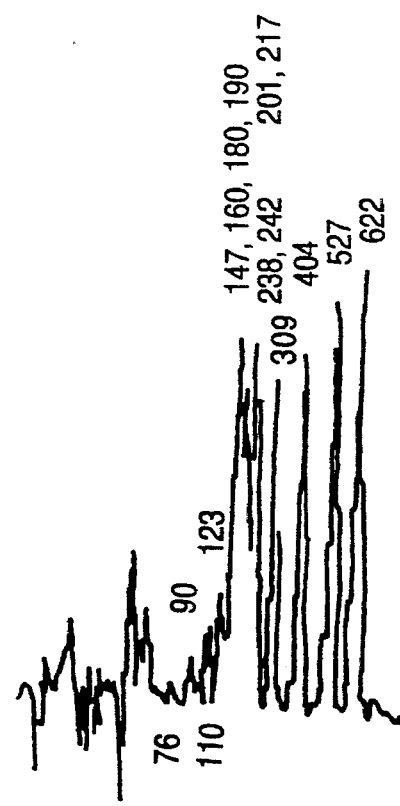
FIG. 11 shows an electropherogram of a separation of double stranded DNA fragments (size range: 76 base pairs to 622 base pairs) by capillary electrophoresis using the copolymer formulation described in Example 1.

Example 7 below describes CE electrophoresis of a double-stranded DNA digest (pBR322 digested to completion with Msp I) in accordance with the method of the invention. The DNA sample contains size fragments ranging from 26–622 basepairs. The copolymer matrix medium is the PEG/stearamide copolymer formed in Example 1, and illustrated in FIG. 4. The PEG polymer segment in the copolymer has a molecular weight of about 2,000 daltons, corresponding to PEG segments having about 136 chain atoms. The electropherogram of the fractionated sample is shown in FIG. 11.

Figure 12:
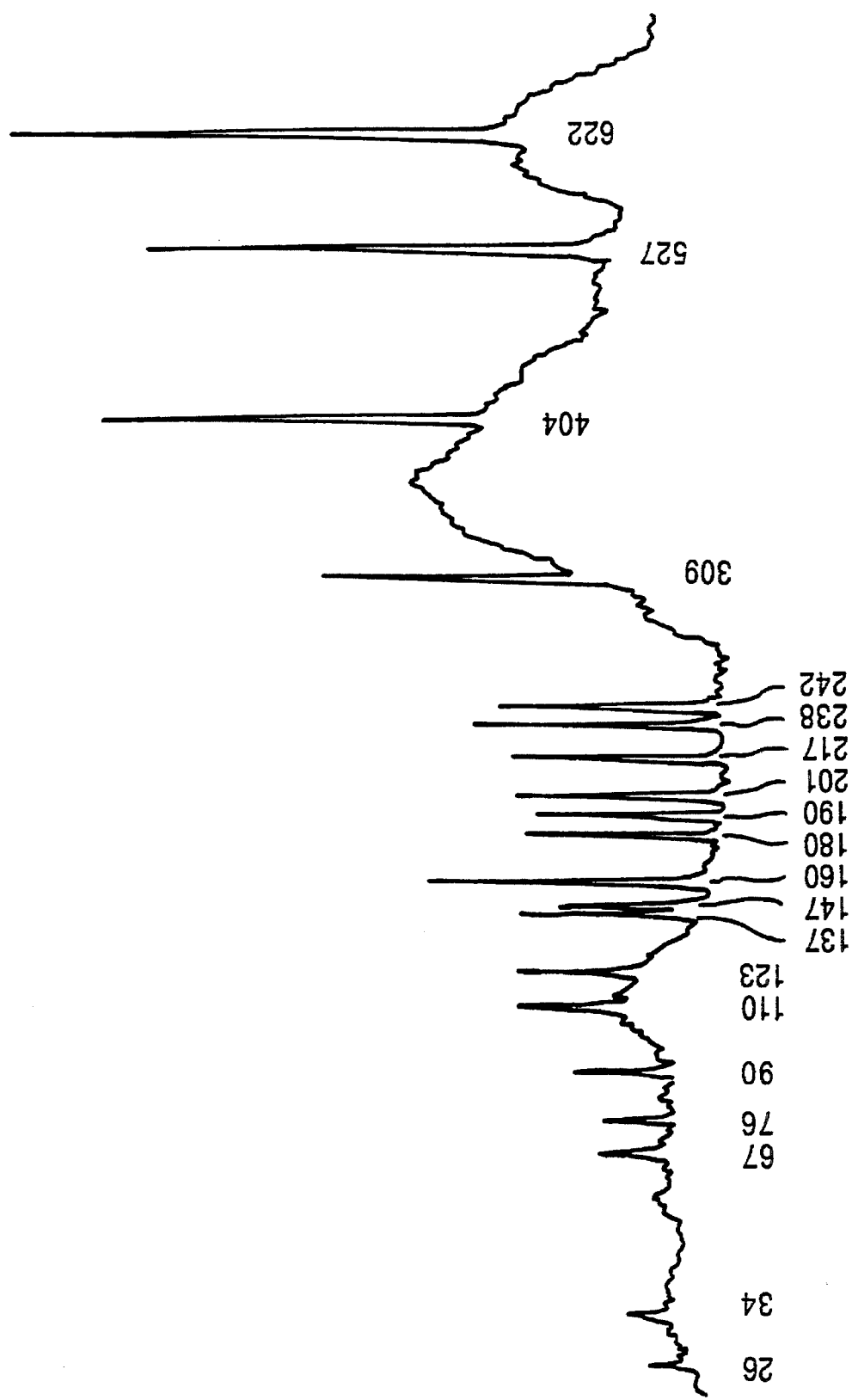
FIG. 12 shows an electropherogram of a separation of double stranded DNA fragments (size range: 26 base pairs to 622 base pairs) by capillary electrophoresis using the copolymer formulation described in Example 4.

Example 8 describes a similar CE electrophoresis run, except that the copolymer matrix was the PEG/fluorinated copolymer prepared as in Examples 2 and 3, and illustrated in FIG. 5. This copolymer is composed of PEG segments of molecular weight 3350 (corresponding to PEG segments having about 228 chain atoms), and $C_4F_9$ hydrophobic segments. The electropherogram is seen in FIG. 12. A comparison of the DNA separation with that in FIG. 11 demonstrates the superiority, for fragment separation by CE electrophoresis, of a copolymer formed with a fluorinated hydrophobic polymer segment.

Figure 13:
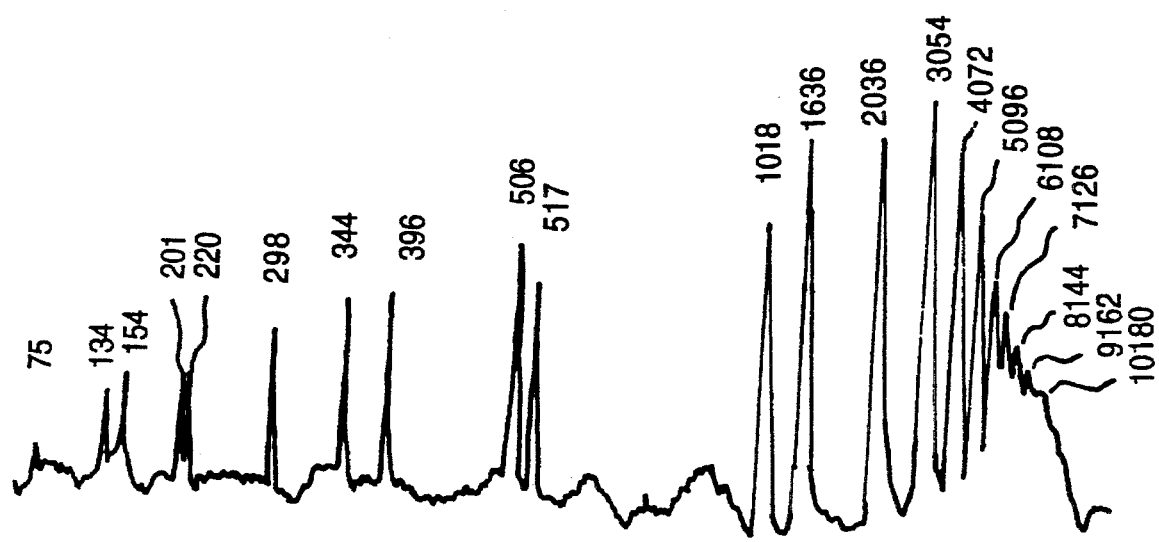
FIG. 13 shows an electropherogram of a separation of double stranded DNA fragments (size range: 75 base pairs to 10,200 base pairs) by capillary electrophoresis using the copolymer formulation described in Example 6.

Example 9 below describes CE electrophoresis of large DNA fragments (a 1 kb ladder purchased from Bethesda Research Labs, Gaithersberg, Md.), in accordance with the method of the invention. This copolymer matrix employed in the method is described in Example 6, and is composed of PEG segments of molecular weight 15,000 daltons (about 1022 chain atoms in the PEG segments) and $C_4F_9$ hydrophobic segments. The electropherogram is seen in FIG. 13. As seen, the matrix is effective in separating DNA fragments up to 10 kilobases in size. More generally, for separating DNA fragments with sizes greater than about 1,000 basepairs, the hydrophilic polymer should have a chain length of between about 500–1,000 or larger.

At the other end of the size scale, for DNA sequence analysis, it is necessary to resolve single-stranded oligomers differing from one another by one nucleotide base. The ability of the present method to achieve resolution of this type is illustrated in the method described in Example 10.

Figure 14:
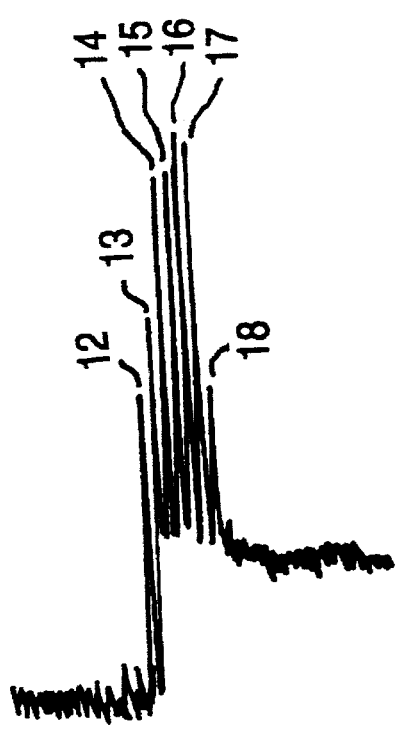
FIG. 14 illustrates an electropherogram of a separation of single stranded DNA fragments (size range: 12 to 18 nucleotides) by capillary electrophoresis using the copolymer formulation described in Example 5.

Here the sample consists of single-stranded poly(dA) fragments with sizes of 12–18 bases. The sample was separated by CE on a comb copolymer matrix as prepared in Example 5, i.e., where the PEG polymer segment is a 1400 dalton polymer (PEG chain length of about 95 atoms), and the hydrophobic segment is a $C_4F_9$ segment. The electropherogram of the separated material is shown in FIG. 14. As seen, each of the 7 peaks in the sample is cleanly resolved.

Figure 15:
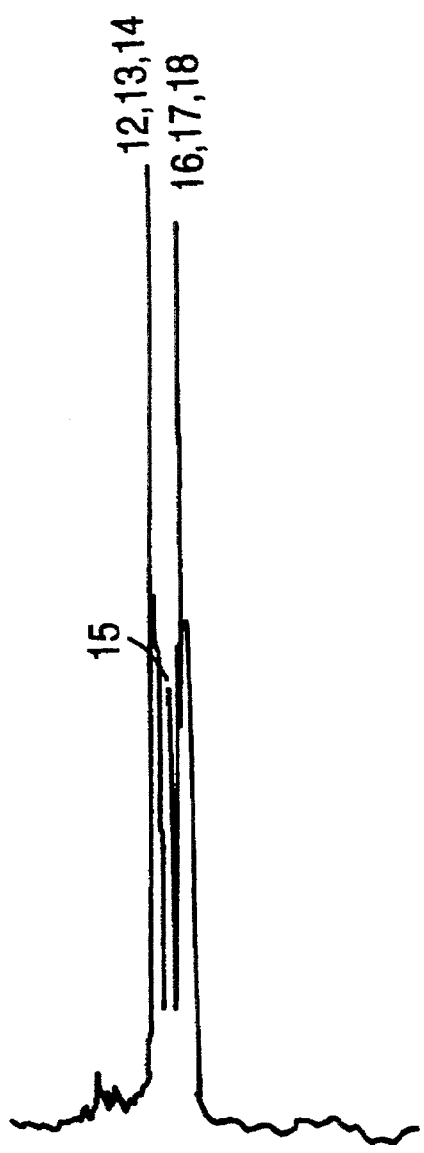
FIG. 15 illustrates an electropherogram of a separation of single stranded DNA fragments (size range: 12 to 18 nucleotides) by capillary electrophoresis using the copolymer formulation described in Example 4.
Figure 16A:
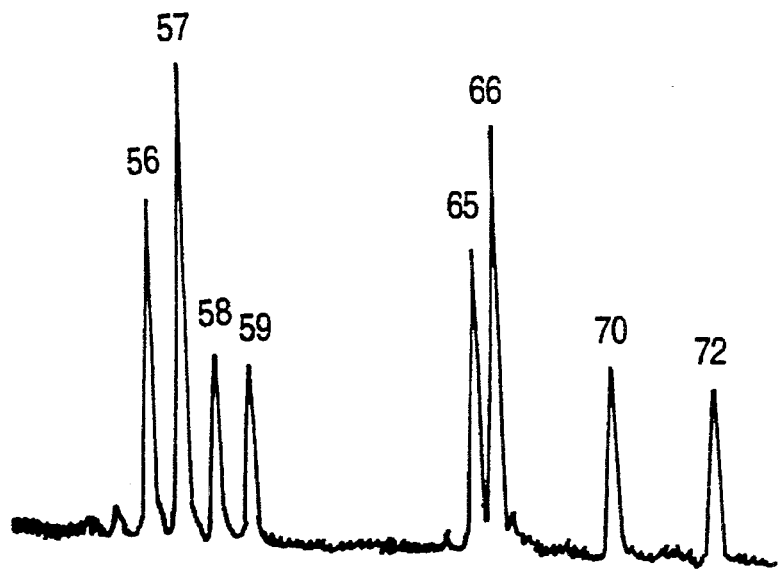
FIGS. 16A–16E illustrates an electropherogram of a separation of DNA sequencing primer extension products, labeled with fluorescein, from an M13mp18 template by capillary electrophoresis using the copolymer formulation described in Example 3 (Carbowax 3350/C4F9 diol)
Figure 16B:
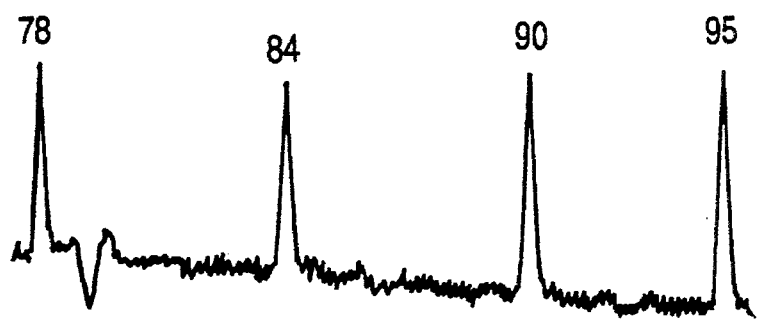
Figure 16C:
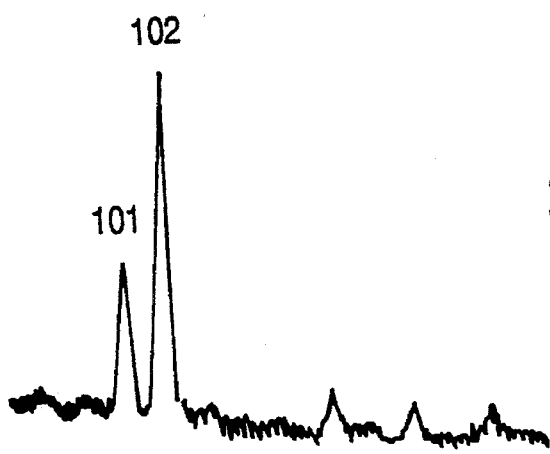
Figure 16D:
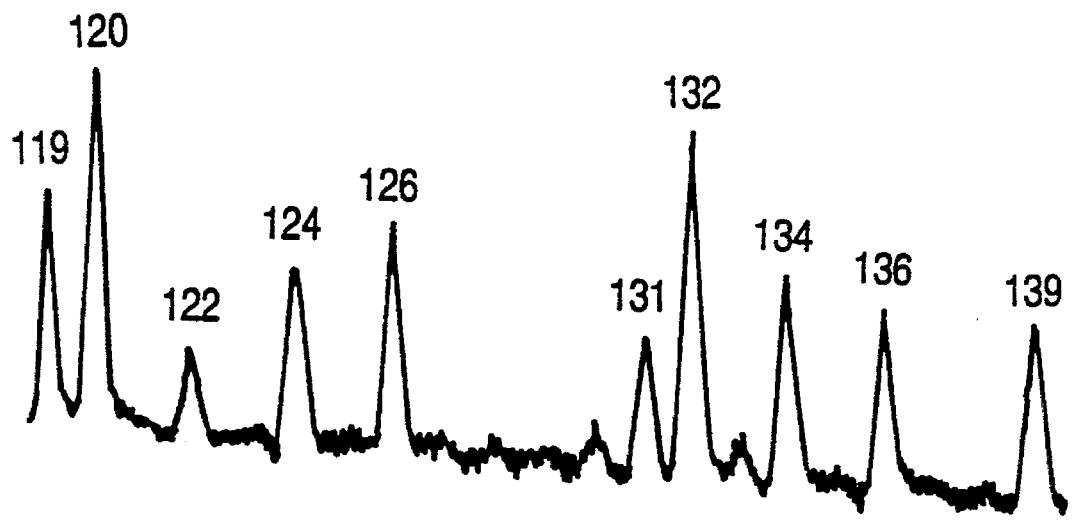
Figure 16E:
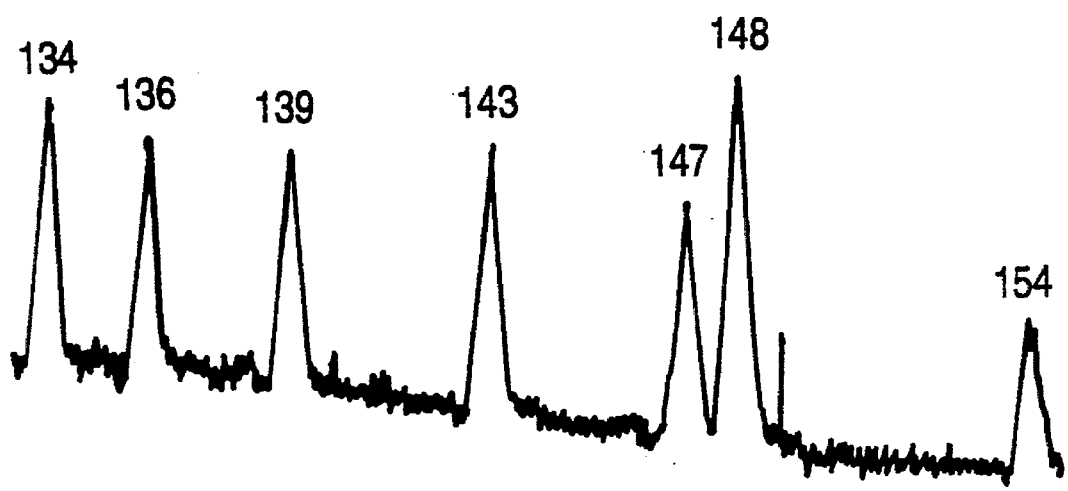

The same poly(dA) sample material from above was also separated on a CE comb copolymer formed of PEG (4600 dalton, or PEG chain length of about 313 atoms) and $C_4F_9$ segments. The electropherogram, shown in FIG. 15, shows poorer resolution of the small single-stranded fragments. The results illustrate the ability to tailor the copolymer for optimal separation characteristics for given sizes of sample molecules to be separated. In particular, for fractionating DNA fragments in a selected size range of less than about 100 bases or basepairs, the comb hydrophilic polymer may have a polymer segment length of less than about 100 chain atoms.

The ability to fractionate intermediate size DNA fragments, i.e., fragments in the 50–150 basepair size range is illustrated by the method described in Example 12. Here DNA sequencing extension products terminating in ddC and labeled with fluorescein were run on a copolymer matrix formed with a PEG 3350 (228 PEG chain length) and $C_4F_9$ hydrophobic chain segments, under denaturing conditions, as described in Example 3. The electropherogram is broken into five regions, identified by FIGS. 16A–16E. As seen, the method is capable of easily separating single-stranded DNA fragments which differ by one base throughout the range of sizes from 56 to 154 bases.

FIGS. 17A–17G illustrate the ability of the present method to provide single-base resolution of DNA-fragments using star copolymers of the invention. In this study, CE matrices containing copolymers of the type shown at FIG. 1F were used to separate single-stranded DNA fragments varying in length from about 30 bases to about 700 bases in length. The copolymers were composed of a PEG chain of defined length (8,000–35,000 MW; about 545–2400 chain atoms) having a selected fluorocarbon or hydrocarbon hydrophobic segment at each end.

The resolution provided by each matrix was assessed by plotting peak width at half-height (circles) and peak interval (fractional time interval between a given peak and a hypothetical peak of a fragment one base shorter in length) as a function of fragment length (Example 29). The limit of resolution was determined as the fragment length at which the peak width and the peak interval are equal, based on the point of intersection of the curves modeled for the peak width and the peak interval data.

Figure 17A:
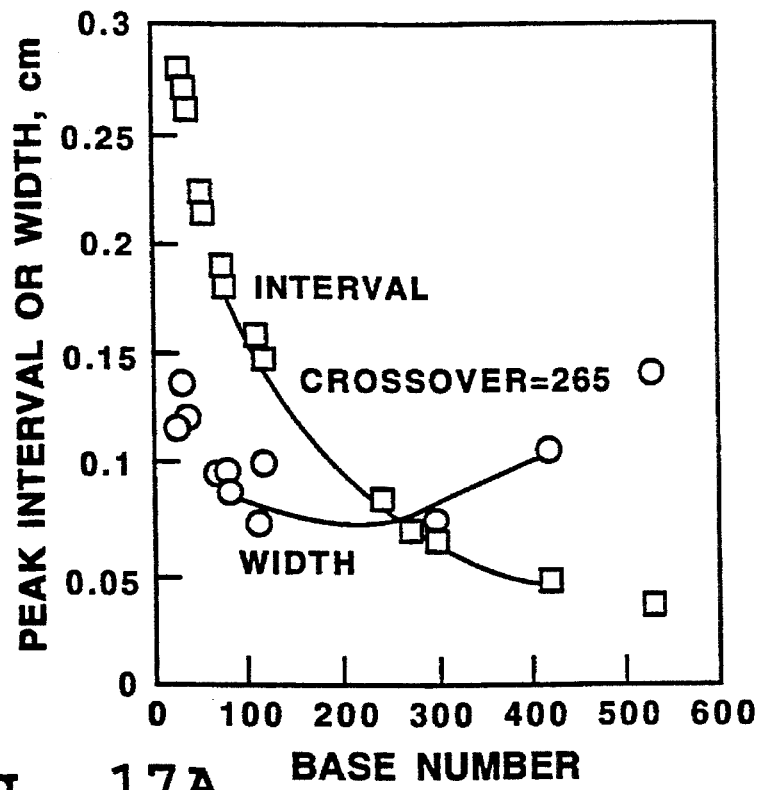
FIGS. 17A–17G show resolution analyses in graphical form for the separation of single-stranded DNA fragments using gels containing exemplary star copolymers of the invention. The graphs show peak width at half-height (circles) and peak interval (fractional time interval between fragments differing in length by one base; squares) as a function of fragment length. The copolymers used in the gels were: PEG-35,000-$(C_6F_{13})_2$, 7% w/v (17A); PEG-35,000-$(C_7F_{15})_2$, 6% w/v (17B); PEG-35,000-$(C_8F_{17})_2$, 5% w/v (17C); PEG-35,000-$(C_{10}F_{21})_2$, 5% w/v (17D); PEG-8,000-$(C_7F_{15})_2$, 5% (17E); PEG-35,000-$(C_{16}H_{33})_2$, 5% (17F); and a 1:1 (w:w) mixture of PEG-35,000-$(C_6F_{13})_2$ and PEG-35,000-$(C_8F_{17})_2$ copolymers, 7% w/v total concentration (17G).

With reference to FIG. 17A and Example 22, the mixture of DNA fragments noted above was separated using the PEG-35,000-$(C_6F_{13})_2$ copolymer synthesized in Example 16. As can be seen from the figure, the matrix provided single base resolution for fragments between about 30 and about 265 bases in length.

Figure 17B:
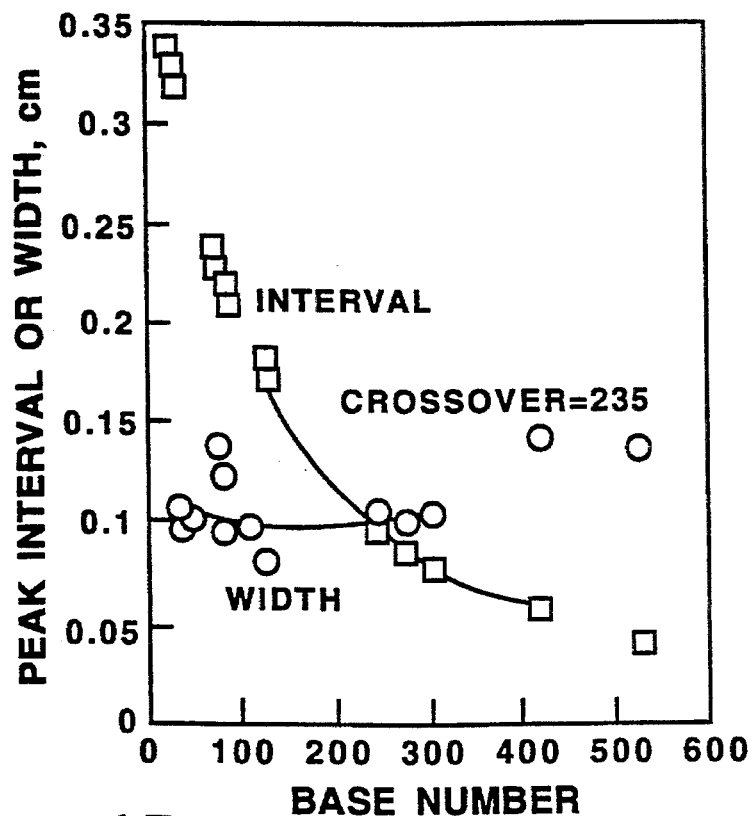
Figure 17C:
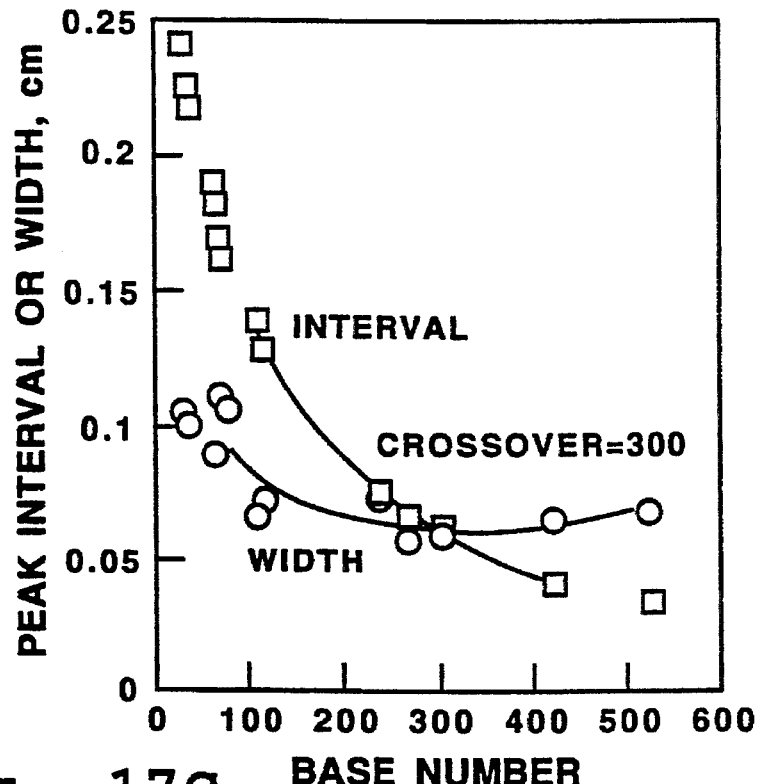
Figure 17D:
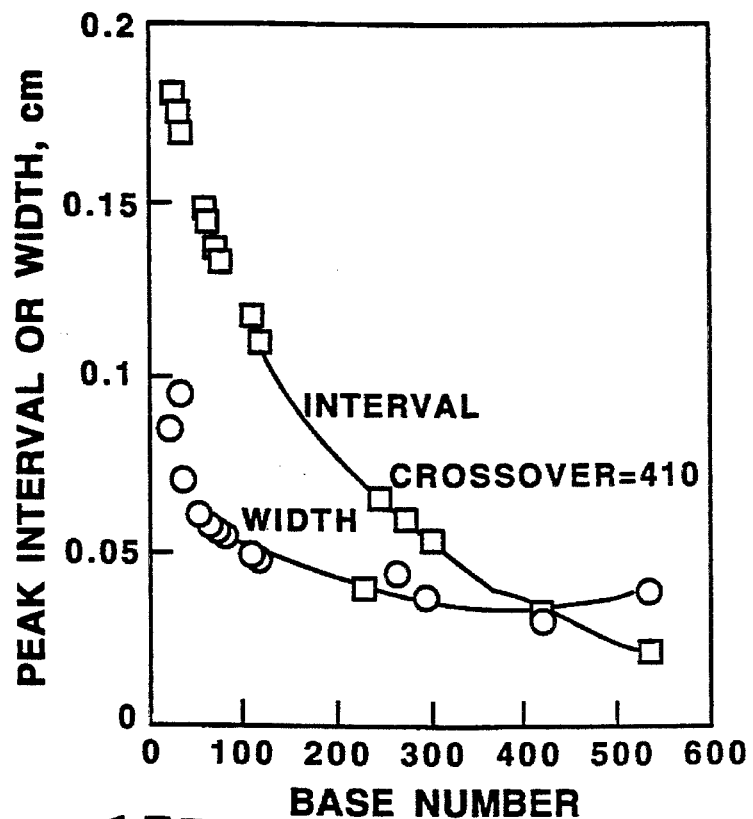

FIGS. 17B–17D show resolution analyses of CE separations of the same DNA fragment mixture used in FIG. 17A, using matrices containing copolymers with longer hydrophobic segments (Example 23–25). Use of a copolymer containing $C_7F_{15}$ segments (FIG. 17B) instead of $C_6F_{13}$ segments afforded about the same resolution as seen in FIG. 17A. A copolymer containing $C_8F_{17}$ segments provided greater resolution, i.e., single-base resolution for fragments between about 30 and about 300 bases in length, as seen in FIG. 7C. $C_{10}F_{21}$ segments provided yet higher resolution, i.e., single base resolution for fragments between about 30 and about 410 bases in length (FIG. 7D).

Figure 17E:
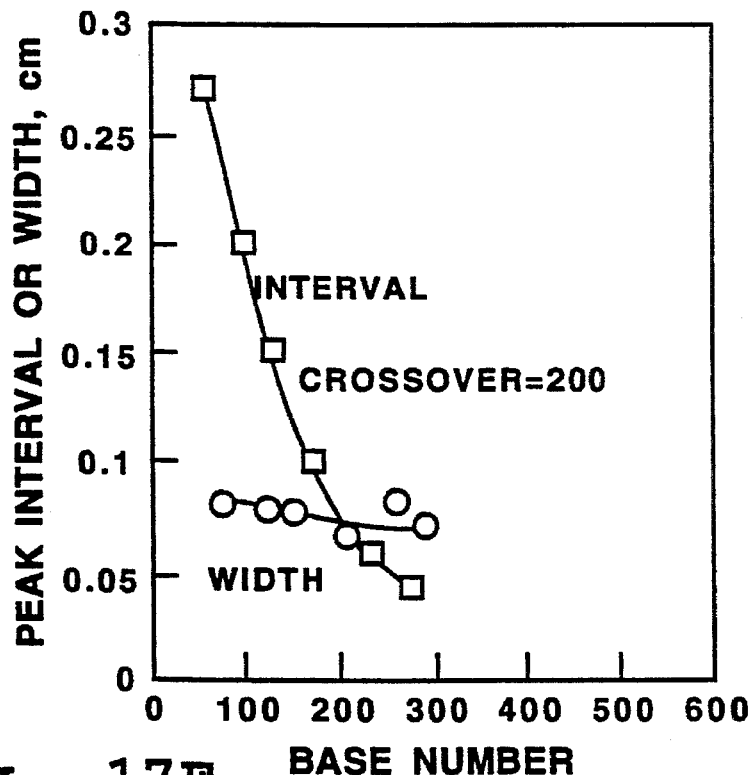

The same DNA fragment mixture was also separated in a CE matrix containing the PEG-8,000-$(C_7F_{15})_2$ polymer prepared in Example 20 (FIG. 17E), to assess the effect of reducing the spacing between the hydrophobic segments. As can be seen by comparison with FIG. 17B, use of PEG-8,000 instead of PEG-35,000 resulted in somewhat lower resolution, i.e., single base resolution for fragments up to about 200 bases in length (FIG. 17E).

Figure 17F:
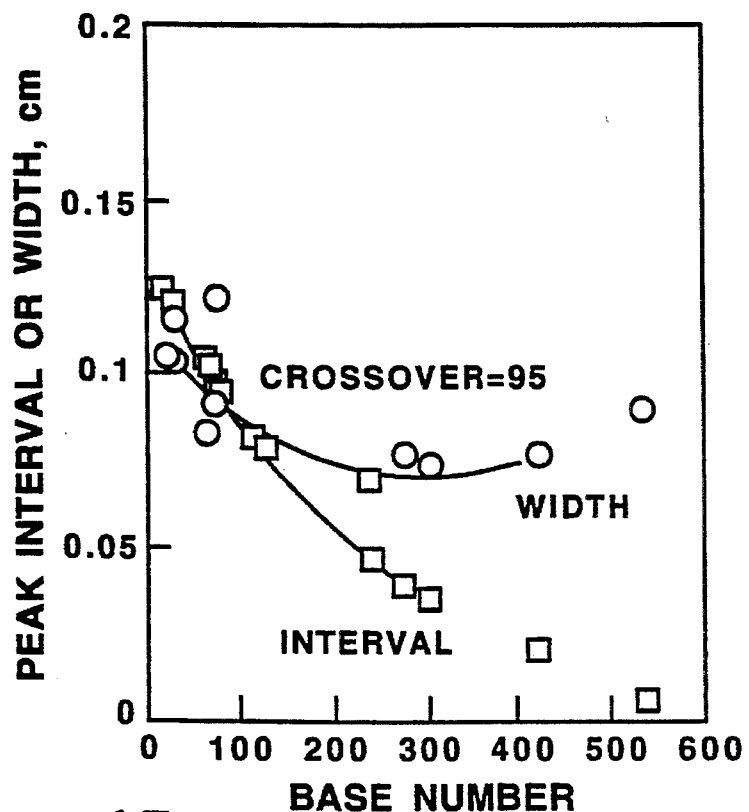

FIG. 17F shows the resolution analysis of a DNA fragment separation in a matrix containing the PEG-35,000-$(C_{16}H_{33})_2$ copolymer prepared in Example 21. As can be seen from the figure, single base resolution was obtained only for fragments of about 30 to about 95 bases in length. This result illustrates the superiority of a copolymer formed with fluorinated hydrophobic polymer segments.

The results shown in FIGS. 17A–17F also illustrate how the lengths of the hydrophilic and hydrophobic segments in the copolymers of the invention can be modified to optimize DNA fragment resolution.

More generally, for use in achieving single-base resolution of single-stranded DNA fragments of between about 30 and about 200 bases in length, and preferably between about 30 and about 400 bases in length, or greater, the copolymers of the invention are formed of contiguous linear hydrophilic polymer segments having a selected combined length of between about 100–4,000 backbone atoms, and hydrophobic polymer segments attached at each of the free ends of the hydrophilic segment(s).

In addition to separation matrices such as illustrated above, which contain homogeneous copolymer mixtures (i.e., copolymers formed from a single copolymer type), the invention also contemplates heterogeneous copolymer mixtures formed from copolymers having hydrophilic segments which are substantially equal in length, but whose hydrophobic segments are different in length. Matrices formed with such copolymer mixtures may lead to improved resolution and viscosity characteristics, relative to matrices formed with homogeneous copolymers. In particular, low viscosity is usually desirable to facilitate loading of the copolymer matrix into a capillary tube.

Figure 17G:
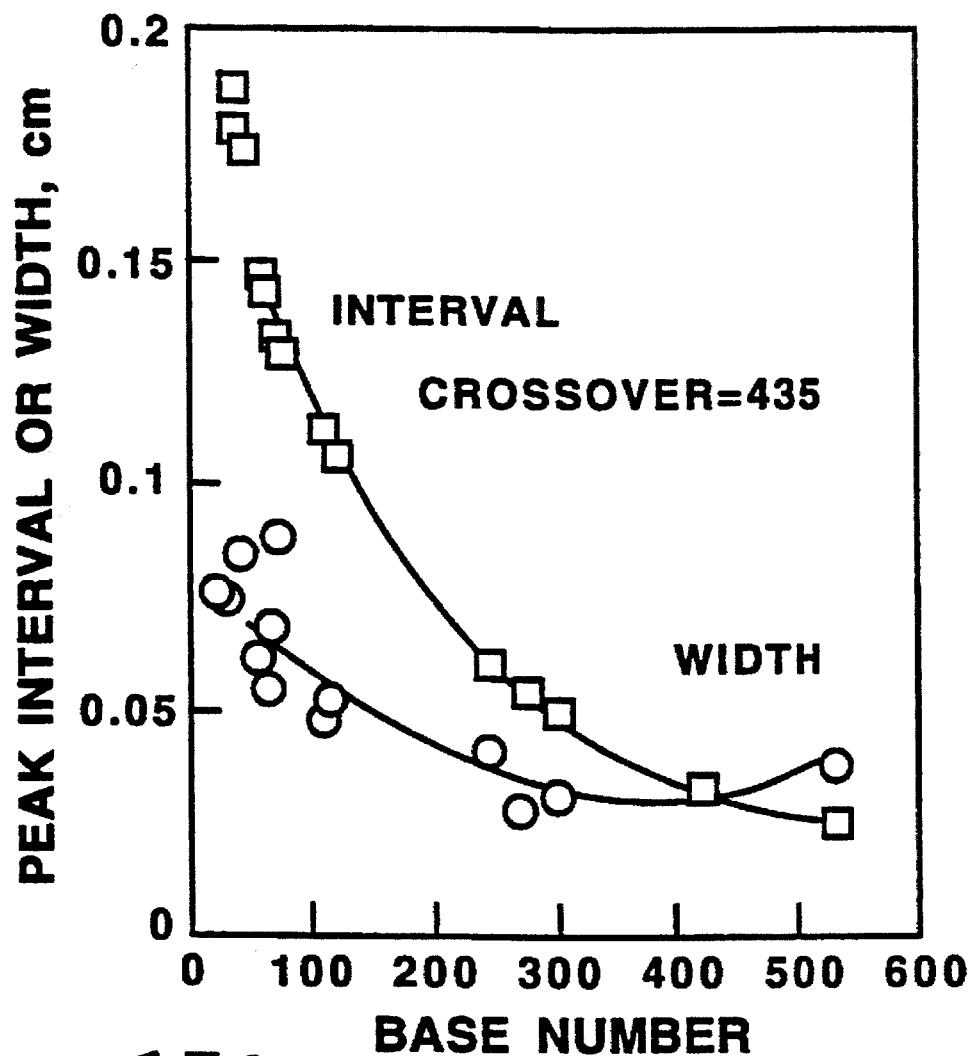

Example 28 describes a study in which electrophoresis was carried out using a 1:1 mixture (7% w/v total concentration) of the PEG-35,000-$(C_6F_{13})_2$ and PEG-35,000-$C_8F_{17}$ copolymers mentioned above (i.e., a 1:1 mixture of copolymers having equal length hydrophilic polymer segments, but different length hydrophobic segments). FIG. 17G shows that this matrix provides a limit of resolution of 435 bases, which is significantly better than the limit of resolution obtained with the PEG-35,000-$C_6F_{13}$ copolymer alone (see FIG. 17A, Example 24), and is comparable to the limit of resolution provided by the PEG-35,000-$C_8F_{17}$ copolymer alone (FIG. 17C).

Table 1 shows viscosities measured for electrophoretic separation matrices formed with PEG-35,000-$(C_6F_{13})_2$ alone (Example 22), PEG-8,000-$(C_7F_{15})_2$ alone (Example 23), PEG-35,000-$C_8F_{17}$ alone (Example 24), and a 1:1 mixture of the PEG-35,000-$(C_6F_{13})_2$ and PEG-35,000-$C_8F_{17}$ copolymers (Example 28). In each matrix, the total copolymer concentration was 7% (w/v).

TABLE 1

| Sample | Spindle Speed | Viscosity (cps) |
| --- | --- | --- |
| (C6/35,000) | 5 | 3200 |

TABLE 1-continued

| Sample | Spindle Speed | Viscosity (cps) |
|---|---|---|
|  | 20 | 3000 |
| (C7/35,000) | 5 | 114,000 |
|  | 20 | 100,000 |
| (C8/35,000) | 5 | 191,000 |
|  | 20 | 160,000 |
| (C6/35,000– C8/35,000) | 5 | 36,600 |
|  | 20 | 36,400 |

Viscosities were measured at the spindle speeds indicated, using a Brookfield MBN Viscometer (Brookfield Engineering Labs, Stoughton, Maine) equipped with a number 7 spindle.

As can be seen from Table 1, the viscosity of the matrix containing a 1:1 mixture of the $C_6F_{13}$- and $C_8F_{17}$-containing copolymers was significantly lower (at a copolymer concentration of 7% w/v) than the viscosities measured for matrices formed by the PEG-35,000-$(C_8F_{17})_2$ copolymer or the PEG-35,000-$(C_7F_{15})_2$ copolymer alone. These results illustrate how including same-length copolymers having shorter hydrophobic segments (in this case, $C_6F_{13}$ segments) can lead to a decrease in viscosity without a significant reduction in resolution (compared to using the $C_8F_{17}$ copolymer alone).

More generally, for separation of single- and double-stranded nucleic acid fragments in the 100–1,000 base or basepair range, the hydrophobic polymer segments in the star copolymers should be spaced at substantially uniform segment lengths from one another via intervening hydrophilic segments (e.g., a PEG chain) whose combined lengths total between about 100–4,000 chain atoms. In one embodiment, the hydrophilic segments are polyethylene glycol segments, and the hydrophobic segments are fluorinated hydrocarbon chains.

The electrophoretic method of the invention can be employed for fractionating peptides and proteins over a wide size range, from small peptides to proteins of molecular weight up to 100,000 daltons or greater. Experiments carried out in support of the invention indicate that electrophoretic separation of proteins is based on a sieving effect in which the molecules are retarded, in passing through the matrix, by the polymer mesh forming the matrix, with larger polypeptides migrating more slowly through the matrix than smaller peptides (with a similar charge density) in an electric field.

The copolymer matrix of the invention is also useful for capillary or preparative-tube isoelectric focusing (IEF), in providing a stable matrix which can be expelled in intact form from the tube after separation of sample components on the pH gradient.

The supported matrix used in carrying out the IEF method is prepared according to the general guidelines above, substituting a standard IEF ampholyte solution for the electrolyte solution used in an electrophoresis matrix. Ampholyte solutions for producing a range of pH gradients, on equilibration in an electric field, are well known.

The type, molecular weight, and concentration of polymer are less critical than in electrophoretic separation, since the polymer matrix does not function as a separation medium. Rather, the polymer composition is selected to (a) minimize band spreading after the electric field is removed, and (b) to facilitate removal of the matrix from the tube after equilibrium is reached. Typically these objective are met in a relatively high matrix viscosities. However, for separation of high molecular weight proteins and nucleic acids, the viscosity must be kept low enough to allow free migration of the molecular species in the matrix.

Sample loading, voltage settings, and run times are carried out conventionally. Typically the sample contains proteins or peptides which are readily separable, on the basis of different isoelectric points, on the selected pH gradient. After equilibrium is reached, the tube may be removed from the system and scanned. Alternatively, and according to an important advantage of the method, the matrix can be expelled in intact form from the tube, for analysis of separated bands in the matrix.

The method enhances the resolution of bands which can be achieved by IEF, since band spreading and wall distortion effects, which smear separated bands when a low-viscosity medium is drawn from the tube, are eliminated. At the same time, the matrix provides the advantages of a low-viscosity medium in that the pH gradient can be expelled from the tube readily for analysis of the separated molecular components. The expelled matrix also allows for analysis by autoradiography or blotting techniques.

From the foregoing, it can be appreciated how various objects and features of the invention are met. The copolymer used forming the separation matrix of the invention can be constructed around a variety of architectures, and with easily varied hydrophilic segment lengths, for optimal separation of biomolecules in a given size range.

The polymer matrix material is readily introduced into and removed from an electrophoresis support matrix, and thus avoid problems of polymer crosslinking, and matrix removal from electrophoresis supports. This ability to introduce and remove the matrix under moderate pressure is particularly advantageous in capillary electrophoresis.

The copolymer matrix gives high (single-base) resolution of DNA samples over a wide size range, and the hydrophilic polymer size can be selected to optimize resolution of different sizes of biomolecules.

The following examples are presented to illustrate the invention and do not limit in any way the scope of the invention.

MATERIALS

The reagents and solvents employed in the examples below were purchased from Aldrich Chemical Company, Milwaukee, WIS., unless otherwise noted. The 2-$(C_4F_9C_2H_4)$propane-1,3-diol hydrophobe monomer was prepared from PFEBI Fluorointermediate (purchased from DuPont Company, Chemicals and Pigments Department, Wilmington, Del.) and diethyl malonate according to DuPont U.S. Pat. No. 3,504,016. The Jeffamine 2001 hydrophile was purchased from Texaco Chemical Company, Houston, Tex. The polyethylene glycol hydrophiles were purchased from Union Carbide, Industrial Chemicals Division, Danbury, Conn., under their Carbowax trade name.

GC capillary tubing (50 micron ID fused silica with DB-1 coating, purchased from J and W Scientific, Folsom, Calif.; cat. #126–1013) was used to demonstrate electrophoretic separating ability of the copolymer formulations. All electrophoresis experiments were performed in 50 cm long capillary tubes that had a detection window burned through the polyimide coating 28 cm from the cathode end of the tube. After the tubes were filled with matrix, DNA samples were electrokinetically injected at the cathode end at 5 kV for 2 to 10 seconds. The electrophoresis experiments were run with buffer chambers that were filled with the exact ion compositions that were used to prepare the matrices; copolymers were excluded from the buffer chambers.

Electrophoresis experiments that used UV absorbance for DNA detection were run on an Applied Biosystems Model 270A capillary electrophoresis instrument, with the UV detector set at 260 nm.

Electrophoresis experiments that used fluorescence emission for DNA detection were run on an apparatus that consisted of: a multi-line 40 mwatt argon-ion laser (purchased from National Laser Company, Salt Lake City, Utah) excitation system whose initial beam was focused to 20 micron at the capillary with a 5 cm focal length positive lens; and a photomultiplier tube detection system where the emitted light was collected with a 1 cm focal length, f/0.7 aspheric lens and directed to a diffraction grating (purchased from Jarrel-Ash, ANASPEC, Acton, Mass.: 985-05-20-22; 1180 rulings/mm, blazed at 500 nm) so that the emission wavelength of interest could be selected for the photomultiplier tube. The laser beam, capillary tube, and collection axes were all perpendicular to each other.

EXAMPLE 1

A polyethylene glycol oligomer (PEG) having terminal amino groups (Jeffamine 2001) was converted to its bisurethane oligomer. Thermal elimination of phenol converted the bisurethane into its bisisocyanate in the presence of a hydrocarbon diol formed the target PEG-hydrocarbon polyurethane copolymer.

Thus, 21.6 g of Jeffamine 2001 (nominal M. W. 2300) was dissolved in 150 mL of ethyl acetate. To this was added 70 mL of a solution of 1:1 20% sodium hydroxide:brine. With rapid stirring, 4 mL of phenyl chloroformate were added dropwise over 10 minutes. After stirring for 1 hour at room temperature, the ethyl acetate layer was dried with anhydrous sodium sulfate, filtered, evaporated under reduced pressure, and evacuated at high vacuum yielding 24.7 g of bisurethane (nominal M. W. 2539) as a waxy solid.

The bisurethane oligomer (9,866 g, 3,886 mMol) was combined with trioctylamine (2.75 g, 7.77 mMol), DMAP (4.0 mg), and bis-N,N-(2-hydroxyethyl)stearamide (1,444 g, 3.886 mMol). The mixture was placed under high vacuum and heated to 140° C. with stirring for 2 hours. The mixture was then cooled to room temperature to give two layers. The upper layer was removed, and the lower layer was purified by extracting with four 40 mL portions of refluxing hexane, followed by twice refluxing with 100 mL portions of methyl t-butyl ether, cooling to room temperature, and decanting the ether. Evacuation under high vacuum yielded 10.0 g of white wax PEG/hydrocarbon copolymer that, upon the addition of water, swelled into a homogeneous, flowable, gel-like solution.

EXAMPLE 2

Onto 1.92 g (5.96 mMol) of 2-($C_4F_9C_2H_4$)propane-1,3-diol was distilled 10 mL of isopherone diisocyanate (80° C. at 0.1 mm). After stirring for 24 hr. under high vacuum in an 80° C. oil bath, most of the excess diisocyanate was distilled off by increasing the oil bath temperature to 95° C. The clear residue was taken into 40 mL of dry refluxing hexane, the solution was cooled to −15° C., and the supernatant was decanted from the oily insoluble residue. The residue was treated with hexane as above two more times, and then evacuated for 4 hr. at room temperature yielding 3.80 g of bisisocyanate as a white foam.

EXAMPLE 3

To a homogeneous a mixture of 1,000 gram of bisisocyanate (1.3055 mMol) from example 2, 4.4053 g of Carbowax 3350 (dried for 3 hr. at 110° C. at high vacuum), and 16 mL of dry toluene, was added 47 microliters of a solution prepared from 0.5 g of dibutyl tin dilaurate dissolved in 2 mL of dry toluene. The solution was heated for 2 hr. at 80° C. under an argon atmosphere, and then diluted with 150 mL of hexane. The rubbery precipitate was triturated three times with 100 mL portions of refluxing methyl t-butly ether, three times with 100 mL portions of refluxing hexane, and evacuated for 12 hr. yielding 5.3 g of rubbery solid. The solid swelled in water to form a flowable gel-like homogeneous solution.

EXAMPLE 4

A copolymer of Carbowax 4600 and $C_4F_9$ hydrophobe was prepared exactly as in example 3, using 1.000 g of bisisocyanate from example 2 and 5.9725 g of PEG.

EXAMPLE 5

A copolymer of Carbowax 1400 and $C_4F_9$ hydrophobe was prepared exactly as in example 3, using 1,000 g of bisisocyanate from example 2 and 2,355 g of PEG.

EXAMPLE 6

A copolymer of PEG M. W. 15,000 (purchased from Polysciences, Inc, Warrington, Pa.) and $C_4F_9$ hydrophobe was prepared exactly as in example 3, using 0.1518 g of bisisocyanate from example 2 and 2.9760 g of PEG.

EXAMPLE 7

An electrophoretic separation matrix was prepared by dissolving 0.60 g of hydrocarbon copolymer from example 1 into 10 mL of a of 90 mM phosphoric acid solution, adjusted to pH 8.0 with tris(hydroxymethyl)aminomethane (TRIS), and injecting into a capillary tube. A double stranded DNA digest (pBR322 Msp I, purchased from New England Biolabs, Beverly, Mass.) suspended in distilled water was electrokinetically injected onto the matrix (5 kV/10 sec), and an electrophoresis experiment was performed at 15 kV. An electropherogram using UV absorption for DNA detection is shown in FIG. 11.

EXAMPLE 8

An electrophoretic separation matrix was prepared by dissolving 1.0 g of fluorocarbon copolymer from example 4 in 20 mL of a 50 mM phosphoric acid solution, adjusted to pH 8.0 with TRIS. Using the same sample as in example 7, an electrophoresis experiment was performed at 12 kV using UV absorption for DNA detection, yielding the electropherogram shown in FIG. 12. By comparing FIGS. 11 and 12, the benefits derived from a copolymer having fluorinated hydrocarbon hydrophobic polymer segments, in terms of increased separation between the DNA fragments, and much narrower bands, is seen.

EXAMPLE 9

An electrophoretic separation matrix was prepared by dissolving 0.60 g of fluorocarbon copolymer from example 6 in 10 mL of a 50 mM phosphoric acid solution, adjusted to pH 8.0 with TRIS. Using a double stranded DNA sample consisting of large DNA fragments (1 kB ladder purchased from Bethesda Research Laboratories ●Life Technologies, Inc., Gaithersberg, Md.), an electrophoresis experiment was performed at 10 kV using UV absorption for DNA detection, yielding the electropherogram shown in FIG. 13. This demonstrates the ability of hydrophobic aggregation matrices prepared from long hydrophiles to separate long DNA fragments (out to 10,000 base pairs for PEG 15,000).

EXAMPLE 10

An electrophoretic separation matrix was prepared by dissolving 0.80 g of fluorocarbon copolymer from example 5 in 10 mL of a 25 mM phosphoric acid solution, adjusted to pH 8.0 with TRIS. Using a single stranded DNA sample consisting of poly(dA) fragments from 12 to 18 nucleotides long (purchased from Pharmacia, Piscataway, N.J.), an electrophoresis experiment was performed at 10 kV using UV absorption for DNA detection, yielding the electropherogram shown in FIG. 14.

EXAMPLE 11

An electrophoretic separation matrix was prepared by dissolving 0.80 g of fluorocarbon copolymer from example 4 in 10 mL of a 25 mM phosphoric acid solution, adjusted to pH 8,0 with TRIS. Using the same DNA sample as in example 10, an electrophoresis experiment was performed at 8 kV using UV absorption for DNA detection, yielding the electropherogram shown in FIG. 15. By comparing FIGS. 14 and 15, it can be seen that the copolymer with the shorter hydrophilic chain (PEG 1450) of example 10 gives superior separation of short DNA fragments.

EXAMPLE 12

An electrophoretic separation matrix was prepared by combining 0.25 g of fluorocarbon copolymer from example 3, 1.2 g of urea, 1.5 mL of a solution 0.25M in boric acid and 0.0025M in EDTA that was adjusted to pH 9.0 with tetramethylammonium hydroxide, and 0.66 mL of water. DNA sequencing extension products terminating in dideoxycytidine and labeled with fluorescene were generated from FAM labeled −21 M13 primer (purchased from Applied Biosystems, p/n 401131) and M13mp18 template with Taq polymerase (purchased from Hoffmann-La Roche, Nutley, N.J.). The extension products were precipitated from ethanol, taken into a 5:1 solution of formamide:50 mM EDTA, heated at 90° C. for two minutes, electrokinetically injected onto the matrix (0.5 kV for 60 seconds), and an electrophoresis experiment was performed at 4 kV. An electropherogram is shown, at various stages, in FIGS. 16A–16. From these figures, it can be seen that single base resolution is obtained to at least 150 bases.

EXAMPLE 13

Onto 15 grams of Carbowax 4600, that had been previously been dried at 110° C. for 4 hr. under high vacuum, was distilled 20 mL of isopherone diisocyanate (80° C. at 0.1 mm). After stirring for 24 hr. under high vacuum in an 80° C. oil bath, most of the diisocyanate was distilled off by increasing the oil bath temperature to 95° C. The residue was triturated 7 times with 50 mL portions of dry (over calcium hydride) refluxing hexane. The hexane-insoluble residue was dried overnight under high vacuum, yielding 16.1 g of waxy solid.

EXAMPLE 14

To a homogeneous mixture of 1.0596 grams (0.2102 mMol) of bisisocyanate from example 13, 0.0709 grams (0.2202 mMol) of 2-($C_4F_9C_2H_4$)propane-1,3-diol, and 5 mL of dry (over calcium hydride) toluene was added one drop of dibutyl tin dilaurate. The solution was refluxed for 1 hr. under an argon atmosphere, and then diluted with 50 mL of hexane. The rubbery precipitate was triturated 3 times with 50 mL portions of refluxing hexane, 3 times with 50 mL portions of refluxing methyl t-butyl ether, three times with 50 mL portions of refluxing hexane, and evacuated 12 hr. yielding 1.04 grams of rubbery solid.

EXAMPLE 15

An electrophoretic separation matrix, using fluorocarbon copolymer from example 14, was prepared according to procedure given in Example 8. Using the same DNA sample as in Example 7, and the same electrophoresis conditions described in Example 8, an electropherogram which closely resembles the electropherogram from example 8 (FIG. 12) was observed.

EXAMPLE 16

PEG-35,000-($C_6F_{13}$)$_2$ copolymer. Tridecafluoro-1-octanol ($C_6F_{13}CH_2CH_2OH$, 6.2 g, #17112-4, PCR Incorporated, Gainesville, Fla.) was placed in a preweighed 200 mL round bottom flask equipped with a teflon stirbar. The preweighed flask was placed in a dry-ice acetone bath and used as a receiver for a vacuum distillation setup. A total of about 10 mL of isopherone diisocyanate was distilled onto the alcohol at 0.01 mm/85°–90° C. The resultant solution was purged with argon, sealed with a stopcock/vacuum-takeoff, and stirred overnight in an 80°–90° C. oil bath. The stopcock was then replaced with a short path distillation setup (connecting adapter, vacuum adapter, and receiver), the system was placed under high vacuum (0.01 mm) and the oil bath temperature was raised to 100° C., during which most of the excess diisocyanate was collected. The oily residue was refluxed with 60 mL of dry (over $CaH_2$) hexane until dissolution was complete, after which the flask was sealed with a rubber septum and cooled to −15° C. for 1–2 hours. The supernatant was then decanted quickly (to avoid water condensation in the cold flask) from the oily residue, and the extraction procedure (reflux in 60 mL hexane followed by decanting of cold supernatant) was repeated two more times. The resultant sticky residue was evacuated for several hours, yielding 2.24 g of activated alcohol as a clear liquid.

Onto the activated alcohol from above was distilled 100 mL of dry ethylene glycol dimethylether (directly from $LiAlH_4$) under argon. The resultant solution was poured into a flask containing 20.0 g of 35,000 MW PEG (Fluka Chemical Co., Ronkonkoma, N.Y.) that had been dried for 4 hours at 0.01 mm, in a 100° C. oil bath. The resultant mixture was homogenized under argon with heat, followed by addition of 50 µL of a solution of 0.5 g of dibutyltin dilaurate in 2 mL of dry (over $CaH_2$) hexane. The mixture was refluxed for 2 hours under argon, and then allowed to cool. After the supernatant had been decanted, the white rubbery product was triturated three times with 200 mL portions of refluxing methyl t-butyl ether, and two times with 200 mL portions of refluxing hexane. The product was evacuated overnight, yielding 18.2 g of a tough white solid.

EXAMPLE 17

PEG-35,000-($C_7F_{15}$)$_2$ block copolymer. Pentadecafluoro-1-octanol ($C_7F_{15}CH_2OH$, 14.2 g, Aldrich) was placed in a preweighed 200 mL round bottom flask equipped with a teflon stirbar and reacted with about 40 mL of isopherone diisocyanate as described in Example 16, to yield 13.5 g of activated alcohol. The activated alcohol was dissolved in 48.8 g of dry (over $CaH_2$) toluene, yielding a stock solution of 0.217 g of activated alcohol per gram of toluene solution.

35,000 MW PEG (29.4 g) was dried for 4 hours at 0.01 mm in a 110° C. oil bath. To the dried PEG was added 11.2 g of activated alcohol stock solution and 50 mL of dry (over $CaH_2$) toluene. The resultant mixture was homogenized under argon with heat, followed by addition of 50 µL of a solution of 0.5 g of dibutyltin dilaurate in 2 mL of dry (over CaH2) hexane. The mixture was refluxed for 3 hours under argon, followed by workup as described in Example 16, to give approximately 25 g of a white rubbery solid.

EXAMPLE 18

PEG-35,000-$(C_8F_{17})_2$ copolymer. Heptadecafluoro-1-decanol ($C_8F_{17}CH_2CH_2OH$, 11.05 g, #17113-2, PCR Inc.) and isopherone diisocyanate (approximately 30 mL) were reacted using the procedure described in Example 16, yielding 12.6 g of activated alcohol as a thick oil. The activated alcohol was then dissolved in 99.0 g of dry (over $CaH_2$) toluene, yielding a stock solution of 0.113 g of activated alcohol per g of toluene solution.

35,000 MW PEG (30 g) was dried for 4 hours at 0.01 mm in a 100° C. oil bath. To the dried PEG were added 15 g of activated alcohol stock solution and 50 mL of dry (over $CaH_2$) toluene. The resultant mixture was homogenized under argon with heat, followed by addition of 50 µL of a solution of 0.5 g of dibutyltin dilaurate in 2 mL of dry (over CaH2) hexane. The mixture was refluxed for 3 hours under argon, followed by workup as described in Example 16, to give approximately 30 g of a white rubbery solid.

EXAMPLE 19

PEG-35,000-$(C_{10}F_{21})_2$ copolymer. 10 g of $C_{10}F_{21}CH_2CH_2OH$, (PCR, Inc.) and 50 g isopherone diisocyanate were reacted according to the procedures described in Example 16. After hexane extraction to remove residual isopherone diisocyanate, the product was evacuated for 4 hours, yielding 4.6 g of activated alcohol as colorless crystals.

Onto the activated-alcohol was distilled 400 mL of dry ethylene glycol dimethylether (directly from $LiAlH_4$) under argon. The activated alcohol solution was poured into a flask containing 40 g of dried 35,000 MW PEG. The resultant mixture was homogenized under argon with heat, followed by addition of 50 µL of a solution of 0.5 g of dibutyltin dilaurate in 2 mL of dry (over CaH2) hexane. The mixture was refluxed for 3 hours under argon, followed by workup as described in Example 16, to give 38.2 g of a white rubbery solid.

EXAMPLE 20

PEG-8,000-$(C_7F_{15})_2$ copolymer. 6 g of $C_7F_{15}CH_2OH$ and 40 g isopherone diisocyanate were reacted according to the procedures described in Example 16. After hexane extraction to remove residual isopherone diisocyanate, the product was evacuated for 4 hours, yielding 4.5 g of activated alcohol as a clear oil.

Onto the activated alcohol was distilled 200 mL of dry ethylene glycol dimethylether (directly from $LiAlH_4$) under argon. The activated alcohol solution was poured into a flask containing 20 g of dried 35,000 MW PEG. The resultant mixture was homogenized under argon with heat, followed by addition of 30 µL of a solution of 0.5 g of dibutyltin dilaurate in 2 mL of dry (over $CaH_2$) hexane. The mixture was refluxed for 3 hours under argon, followed by workup as described in Example 16, to give 19 g of a white rubbery solid.

EXAMPLE 21

PEG-35,000-$(C_{16}H_{33})_2$ copolymer. Cetyl alcohol (5.0 g, Aldrich Chemical Co.) and isopherone diisocyanate (approximately 10 mL) were reacted according to the procedures-described in Example 16. After hexane extraction to remove residual isopherone diisocyanate, the product was evacuated for 4 hours, yielding 0.21 g of activated alcohol as a clear oil.

Onto the activated alcohol was distilled 50 mL of dry ethylene glycol dimethylether (directly from $LiAlH_4$) under argon. The activated alcohol solution was poured into a flask containing 6.0 g of dried 35,000 MW PEG. The resultant mixture was homogenized under argon with heat, followed by addition of 20 µL of a solution of 0.5 g of dibutyltin dilaurate in 2 mL of dry (over $CaH_2$) hexane. The mixture was refluxed for 3 hours under argon, followed by workup as described in Example 16, to give 5.8 g of a white rubbery solid.

EXAMPLE 22

The PEG-35,000-$(C_6F_{13})_2$) copolymer from Example 16 was dissolved in 125 mM borate-tetramethylammonium, pH 9.0, containing 1.25 mM disodium ethylenediaminetetraacetate (Na-EDTA) and 40% (w/v) urea, to give a gel having a final copolymer concentration of 7% (w/v). A DB-Wax-coated capillary (50 µm i.d. and 32 cm well/read) was filled with the formulated gel. Dye-labeled DNA fragments (ABI Genescan 1000-FAM) were formulated in 70% formamide containing 3 mM disodium ethylenediaminetetraacetate to a DNA concentration of 4 ng DNA/µl. Sample was introduced into the capillary by electrokinetic injection at 90 volts/cm, 3.1 µA, 24 seconds. The electrophoretic separation was performed at 180 volts/cm. The graph in FIG. 17A shows that DNA fragments which differ in length by a single base are resolved up to about 265 bases.

EXAMPLE 23

ACE gel containing the PEG-35,000-$(C_7F_{15})_2$ copolymer from Example 17 (6% w/v final copolymer concentration) was prepared by the procedure described in Example 21. Dye-labeled DNA fragments (ABI Genescan 1000-FAM) were introduced into the capillary by electrokinetic injection at 90 volts/cm, 3.7 µA, 30 seconds and separated as in Example 21. The graph in FIG. 17B shows that DNA fragments which differ in length by a single base are resolved up to about 230 bases.

EXAMPLE 24

ACE gel containing the PEG-35,000-$(C_8F_{17})_2$ copolymer from Example 18 (5% w/v final copolymer concentration) was prepared by the procedure described in Example 21. Dye-labeled DNA fragments (ABI Genescan 1000-FAM) were introduced into the capillary by electrokinetic injection at 90 volts/cm, 4.1 µA, 18 seconds. The graph in FIG. 17C shows that DNA fragments which differ in length by a single base are resolved up to about 300 bases.

EXAMPLE 25

ACE gel containing the PEG-35,000-$(C_{10}F_{21})_2$ copolymer from Example 19 (5% w/v final copolymer concentration) was prepared by the procedure described in Example 21. Dye-labeled DNA fragments (ABI Genescan 1000-

FAM) were introduced into the capillary by electrokinetic injection at 90 volts/cm. The graph in FIG. 17D shows that DNA fragments which differ in length by a single base are resolved up to about 410 bases.

EXAMPLE 26

ACE gel containing the PEG-8,000-$(C_7F_{15})_2$ copolymer from Example 20 (5% w/v final copolymer concentration) was prepared by the procedure described in Example 21. Dye-labeled DNA fragments (ABI Genescan 1000-FAM) were introduced into the capillary by electrokinetic injection at 90 volts/cm. The graph in FIG. 17E shows that DNA fragments which differ in length by a single base are resolved up to about 200 bases.

EXAMPLE 27

ACE gel containing the PEG-35,000-$(C_{16}H_{33})_2$ copolymer from Example 21 (5% w/v final copolymer concentration) was prepared by the procedure described in Example 21 and used to separate the dye-labeled DNA fragments from Example 21. The graph in FIG. 17F shows that DNA fragments which differ in length by a single base are resolved up to about 95 bases.

EXAMPLE 28

ACE gel containing a 1:1 (w/w) mixture of the PEG-35,000-$(C_6F_{13})_2$ copolymer from Example 16 and the PEG-35,000-$(C_8F_{17})_2$) copolymer from Example 18, 7% (w/v) total concentration (3.5% for each copolymer), was prepared by the procedure described in Example 21 and used to separate the dye-labeled DNA fragments from Example 22. The graph in FIG. 17G shows that DNA fragments which differ in length by a single base are resolved up to about 435 bases.

EXAMPLE 29

The resolution analyses in Examples 22–28 (see FIGS. 17A–17G) were conducted as follows.

The peak width at half height ($W_{1/2}$) for each peak was determined in units of millimeters (mm) according to the equation, $$W_{1/2}=D(t_L-t_T)/t_M,$$

where D is the migration distance in millimeters from the capillary tube inlet to the detector, $t_L$ is the elution time of the leading edge of the peak at half height, $t_T$ is the elution time of the trailing edge of the peak at half height, and $t_M$ is the elution time of the peak at maximum height.

The peak interval (the interval between peaks differing in length by one base) for a peak was determined in units of mm using the equation, $$Int=D[(t_2-t_1)/t_1]/n,$$

where D is as above, t1 is the elution time of the peak of interest, $t_2$ is the elution time of the nearest later eluting peak, and n is the difference in length of the two peaks in units of nucleotide bases.

To determine the resolution of the particular gel matrix used for electrophoretic separation, peak width at half height and peak interval were plotted as a function of fragment length, and each set of data (peak width data; peak interval data) was fitted to a second order polynomial equation determined by linear regression analysis. The resolution of the gel matrix was determined as the point of intersection of the two curves. For example, in FIG. 17A, the limit of resolution of the gel matrix used in the separation medium described in Example 22 occurs at a fragment length of about 265 bases.

Although the invention has been described with respect to specific synthetic methods, compositions, and electrophoretic methods, it will be appreciated that various changes and modification can be made without departing from the invention.

It is claimed:

1. An electrophoresis separation medium comprising
   a matrix of aggregated copolymers in an aqueous medium, said copolymers being formed of contiguous linear hydrophilic polymer segments having a selected combined length, and a hydrophobic polymer segment carried on each of the free ends of the contiguous hydrophilic segments, said medium being characterized by:
   (i) the ability of the medium to effect a high-resolution electrophoretic separation of biopolymer molecules in a defined molecular size range, and
   (ii) a concentration of the copolymer which is above the interpolymeric-aggregation transition concentration, defined by the concentration of copolymer sufficient to produce a marked rise in viscosity of an aqueous dispersion of the copolymer.

2. The medium of claim 1, wherein the linear hydrophilic segments are formed of two hydrophilic segments which are joined at their adjacent ends by a common anchor.

3. The medium of claim 1, wherein the hydrophilic segments are formed of a single linear polymer chain.

4. The medium of claim 1, wherein the hydrophilic segments are polyethyleneglycol segments and the hydrophobic segments are fluorinated hydrocarbon chains.

5. The medium of claim 1, for use in separating single-stranded DNA fragments of between about 30 and about 200 bases in length, wherein the hydrophilic polymer segments have a combined length of between about 100 and about 4,000 backbone atoms.

6. The medium of claim 5, wherein the hydrophilic segments are polyethyleneglycol segments and the hydrophobic segments are fluorinated hydrocarbon chains.

7. An electrophoresis system for separating biopolymers, comprising
   a support defining an elongate channel connectable at opposite ends to opposing polarity terminals of a voltage source, and
   contained within the channel, an electrophoresis separation medium comprising a matrix of aggregated regular alternating copolymers in an aqueous medium, said copolymers being composed of contiguous linear hydrophilic polymer segments having a selected combined length, and a hydrophobic polymer segment carried on each of the free ends of the contiguous hydrophilic segments,
   said medium being characterized by:
   (i) the ability of the medium to effect a high-resolution electrophoretic separation of biopolymer molecules in a defined molecular size range, and
   (ii) a concentration of the copolymer which is above the interpolymeric-aggregation transition concentration, defined by the concentration of copolymer sufficient to produce a marked rise in viscosity of an aqueous dispersion of the copolymer.

8. The system of claim 7, wherein the support is a capillary tube.

9. The system of claim 8, wherein the hydrophilic polymer segments are selected from the group consisting of a polyether, polyester, polysaccharide, polyurethane, polyamides, polysulfonamide, and polysulfoxide.

10. The system of claim 7, wherein the linear hydrophilic segments are formed of two hydrophilic segments which are attached at their adjacent ends to a common anchor.

11. The system of claim 7, wherein the joined hydrophilic segments are formed of a single linear polymer chain.

12. The system of claim 7, wherein the hydrophilic segments are polyethyleneglycol segments and the hydrophobic segments are fluorinated hydrocarbon chains.

13. The system of claim 7, for use in separating single-stranded DNA fragments of between about 30 and about 200 bases in length, wherein the hydrophilic polymer segments having a combined length of between about 100 and about 4,000 backbone atoms.

14. The system of claim 13, wherein the hydrophilic segments are polyethyleneglycol segments and the hydrophobic segments are fluorinated hydrocarbon chains.

15. A method for fractionating a mixture of biopolymer molecules in a selected size range within a matrix contained in a support, comprising:

(a) selecting a regular alternating copolymer having a polymer structure composed of hydrophilic polymer segments having selected, substantially uniform segment lengths, and a plurality of hydrophobic polymer segments carried on and spaced from one another by the hydrophilic polymer segments, (b) dispersing the copolymer in an aqueous medium, at a copolymer concentration which is above the interpolymeric-aggregation transition concentration, defined by the concentration of copolymer sufficient to produce a marked rise in viscosity of an aqueous dispersion of the copolymer, (c) by said dispersing, forming a matrix having the ability to effect a high-resolution electrophoretic separation of biopolymer molecules in a defined molecular size range, (d) placing the matrix in a support defining an elongate channel connectable at opposite ends to opposing polarity terminals of a voltage source, (e) adding the mixture of biopolymer molecules to the matrix at one end of the support, (e) applying an electric field across opposing end regions of the support, to effect electrophoretic migration of the molecules through the matrix, and (f) by said applying, separating different species of molecules within the matrix.

16. The method of claim 15, for use in separating DNA fragments within a selected size range, wherein the copolymers have a comb structure having a backbone composed of linked hydrophilic segments and hydrophobic segments spaced at substantially equal intervals along the backbone, at a selected distance between about 50 and 1,000 backbone chain atoms, for fractionation of DNA fragments in selected size ranges (i) of less than about 100 basepairs, at a selected backbone spacing of about 100 chain atoms, (ii) of greater than about 1,000 basepairs, at a selected backbone spacing between about 500–1,000 chain atoms, and (iii) of sizes between about 100–1,000 basepairs at a selected backbone spacing between about 100–800 chain atoms.

17. The method of claim 16, wherein the copolymer is a comb copolymer in which fluorinated hydrocarbon segments extend outwardly from a backbone composed of linked polyethylene oxide segments.

18. The method of claim 15, wherein the support is a capillary tube.

19. The method of claim 15, wherein the copolymers have a structure selected from the group consisting of:

(a) a comb copolymer structure in which the hydrophobic polymer segments extend outwardly from a backbone composed of linked hydrophilic polymer segments;

(b) a block copolymer structure having an alternating linear sequence of the hydrophilic segments and hydrophobic segments; and (c) a star copolymer structure in which the hydrophobic polymer segments are carried at the distal ends of the hydrophilic polymer segments which are attached at their proximal ends to a common anchor.

20. The method of claim 15, wherein the hydrophilic polymer segments are selected from the group consisting of a polyether, polyester, polysaccharide, polyurethane, polyamide, polysulfonamide, and polysulfoxide.

21. The method of claim 15, wherein the hydrophobic polymer segments are fluorinated hydrocarbon chains.

22. The method of claim 19, wherein the hydrophilic polymer segments are polyethylene oxide segments.

23. The method of claim 15, wherein the copolymers are formed of contiguous linear hydrophilic polymer segments having a selected combined length, and a hydrophobic polymer segment carried on each of the free ends of the hydrophilic segments.

24. The method of claim 23, wherein the linear hydrophilic segments are formed of two hydrophilic segments which are joined at their adjacent ends by a common anchor.

25. The method of claim 23, wherein the hydrophilic segments are formed of a single linear polymer chain.

26. The method of claim 23, wherein the hydrophilic segments are polyethyleneglycol segments and the hydrophobic segments are fluorinated hydrocarbon chains.

27. The method of claim 23, for use in separating single-stranded DNA fragments of between about 30 and about 200 bases in length, wherein the hydrophilic polymer segments have a combined length of between about 100 and about 4,000 backbone atoms.

28. The method of claim 27, wherein the hydrophilic segments are polyethyleneglycol segments and the hydrophobic segments are fluorinated hydrocarbon chains.

* * * * *